(12) United States Patent
Arekar et al.

(10) Patent No.: US 8,785,476 B2
(45) Date of Patent: Jul. 22, 2014

(54) SOLID FORMS OF N-[2,4-BIS(1,1-DIMETHYLETHYL)-5-HYDROXYPHENYL]-1,4-DIHYDRO-4-OXOQUINOLINE-3-CARBOXAMIDE

(71) Applicant: Vertex Pharmaceuticals Incorporated, Cambridge, MA (US)

(72) Inventors: Sneha G. Arekar, Brighton, MA (US); Steven C. Johnston, Litchfield, NH (US); Mariusz Krawiec, Marlborough, MA (US); Ales Medek, Winchester, MA (US); Praveen Mudunuri, Waltham, MA (US); Mark Jeffrey Sullivan, Framingham, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/682,075

(22) Filed: Nov. 20, 2012

(65) Prior Publication Data

US 2013/0079367 A1    Mar. 28, 2013

Related U.S. Application Data

(62) Division of application No. 13/053,172, filed on Mar. 21, 2011, now Pat. No. 8,471,029.

(60) Provisional application No. 61/315,885, filed on Mar. 19, 2010.

(51) Int. Cl.
*C07D 215/56* (2006.01)

(52) U.S. Cl.
USPC .......................................................... 514/312

(58) Field of Classification Search
None
See application file for complete search history.

(56) References Cited

U.S. PATENT DOCUMENTS

2011/0064811 A1    3/2011    Hurter et al.

FOREIGN PATENT DOCUMENTS

| WO | 2006/002421 A2 | 1/2006 |
| WO | 2007/079139 A2 | 7/2007 |
| WO | 2010/108162 A1 | 9/2010 |

OTHER PUBLICATIONS

International Search Report for PCT/US2011/029276, dated Apr. 29, 2011.

*Primary Examiner* — Janet L Andres
*Assistant Examiner* — Timothy R Rozof
(74) *Attorney, Agent, or Firm* — Honigman Miller Schwartz and Cohn LLP; Christopher C. Forbes; Jonathan P. O'Brien

(57) ABSTRACT

The present invention relates to solid state forms of N-[2,4-bis(1,1-dimethylethyl)-5-hydroxyphenyl]-1,4-dihydro-4-oxoquinoline-3-carboxamide (Compound 1), pharmaceutical compositions thereof and methods therewith.

9 Claims, 6 Drawing Sheets

SOLID FORMS OF N-[2,4-BIS(1,1-DIMETHYLETHYL)-5-HYDROXYPHENYL]-1,4-DIHYDRO-4-OXOQUINOLINE-3-CARBOXAMIDE

CLAIM OF PRIORITY

This application is a division of U.S. application Ser. No. 13/053,172, filed Mar. 21, 2011, which claims priority under 35 U.S.C. 119(e) to provisional application Ser. No. 61/315,885, filed on Mar. 19, 2010. The entire contents of each of the above applications are incorporated herein by reference.

TECHNICAL FIELD OF THE INVENTION

The present invention relates to solid state forms of N-[2,4-bis(1,1-dimethylethyl)-5-hydroxyphenyl]-1,4-dihydro-4-oxoquinoline-3-carboxamide, pharmaceutical compositions thereof, and methods therewith.

BACKGROUND OF THE INVENTION

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs, known as potentiators that increase the probability of CFTR channel opening represent one potential therapeutic strategy to treat CF.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl ion channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

N-[2,4-bis(1,1-dimethylethyl)-5-hydroxyphenyl]-1,4-dihydro-4-oxoquinoline-3-carboxamide (Compound 1) is a potent and selective CFTR potentiator of wild-type and mutant (including e.g., ΔF508, R117H, and G551D) forms of human CFTR. Compound 1 is useful for treatment of adult patients with cystic fibrosis and at least one G551D-CFTR allele.

Accordingly, there is a need for stable solid forms of modulators of CFTR activity, such as Compound 1, that can be used to modulate the activity of CFTR in the cell membrane of a mammal.

There is a need for methods of treating CFTR-mediated diseases using such modulators of CFTR activity.

SUMMARY OF THE INVENTION

The present invention relates to solid forms of N-[2,4-bis(1,1-dimethylethyl)-5-hydroxyphenyl]-1,4-dihydro-4-oxoquinoline-3-carboxamide (hereinafter "Compound 1") which has the structure below:

Compound 1

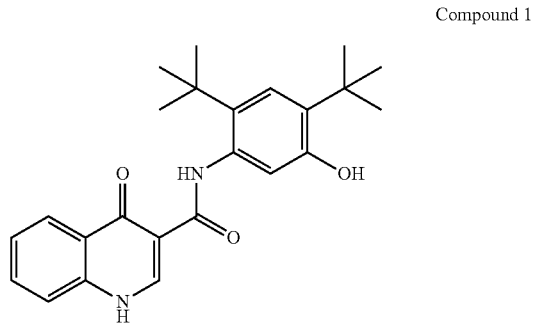 [SMILES: CC(C)(C)c1cc(C(C)(C)C)c(NC(=O)c2c[nH]c3ccccc3c2=O)cc1O]

The solid forms of Compound 1 and pharmaceutically acceptable compositions thereof are useful for treating or lessening the severity of a variety of CFTR mediated diseases. Compound 1 is known as both N-[2,4-bis(1,1-dimethylethyl)-5-hydroxyphenyl]-1,4-dihydro-4-oxoquinoline-3-carboxamide and N-(5-hydroxy-2,4-di-tert-butyl-phenyl)-4-oxo-1H-quinoline-3-carboxamide.

In one aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption, and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In certain embodiments, the disease is cystic fibrosis.

DETAILED DESCRIPTION OF THE INVENTION

Definitions

Figure 1:
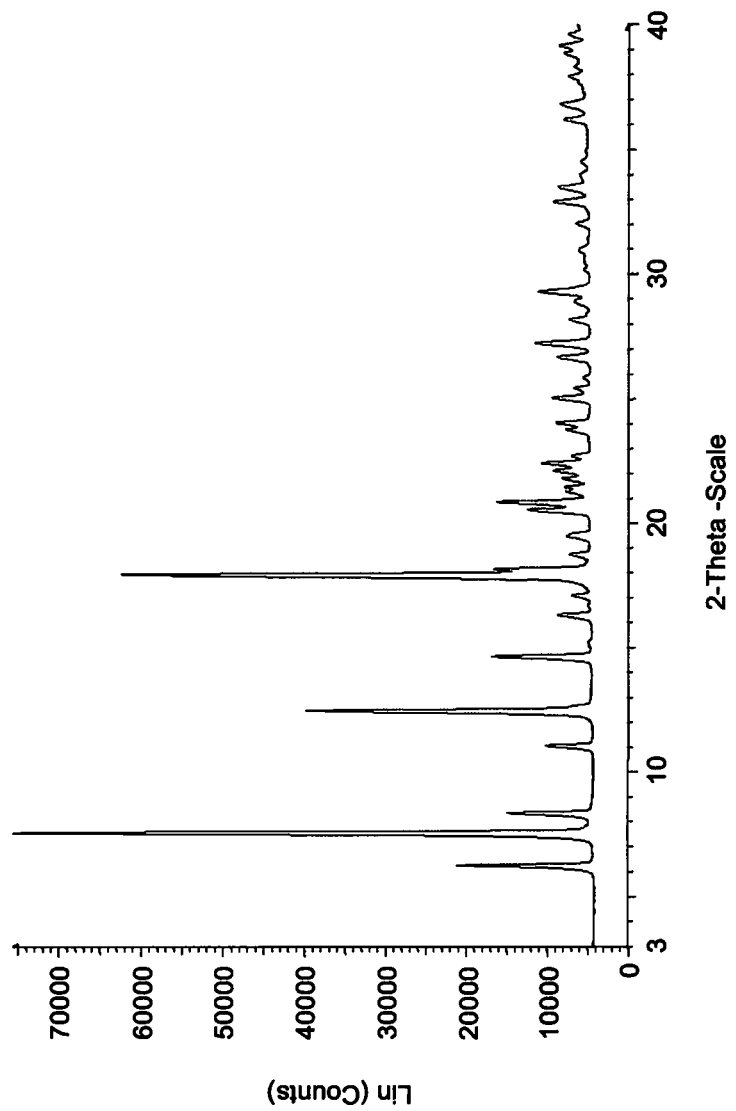
FIG. 1 is an exemplary X-Ray powder diffraction pattern of Form C of Compound 1.

Processes described herein can be used to prepare the compositions of this invention. The amounts and the features of the components used in the processes would be as described herein.

As used herein "crystalline solids" refers to Compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present Compounds are within the scope of the invention. All tautomeric forms of the Compound 1 are included herein. For example, Compound 1 may exist as tautomers, both of which are included herein:

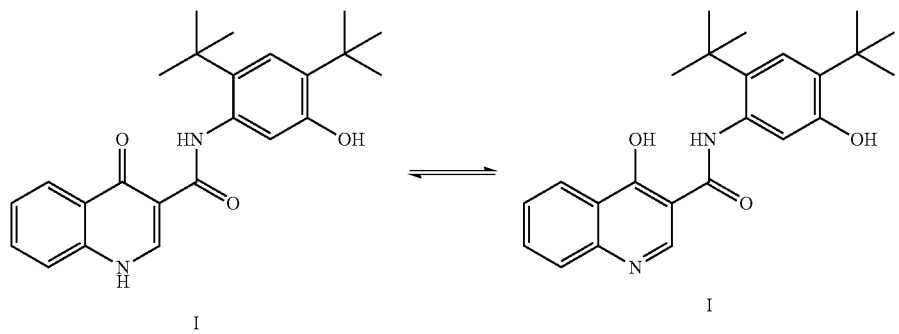

Additionally, unless otherwise stated, structures depicted herein are also meant to include Compounds that differ only in the presence of one or more isotopically enriched atoms. For example, Compound 1, wherein one or more hydrogen atoms are replaced deuterium or tritium, or one or more carbon atoms are replaced by a $^{13}$C- or $^{14}$C-enriched carbon are within the scope of this invention. Such Compounds are useful, for example, as analytical tools, probes in biological assays, or Compounds with improved therapeutic profile.

Solid Form C of Compound 1

XRPD (X-Ray Powder Diffraction)

The XRPD patterns were acquired at room temperature in reflection mode using a Bruker D8 Advance diffractometer equipped with a sealed tube copper source and a Vantec-1 detector. The X-ray generator was operating at a voltage of 40 kV and a current of 40 mA. The data were recorded in a θ-θ scanning mode over the range of 3°-40° 2θ with a step size of 0.014° and the sample spinning at 15 rpm.

In one aspect, the invention includes crystalline N-[2,4-bis(1,1-dimethylethyl)-5-hydroxyphenyl]-1,4-dihydro-4-oxo-quinoline-3-carboxamide (Compound 1) characterized as Form C.

In one embodiment of this aspect, Form C is characterized by a peak having a 2-Theta value from about 6.0 to about 6.4 degrees in an XRPD pattern. In a further embodiment, Form C is characterized by a peak having a 2-Theta value from about 7.3 to about 7.7 degrees in an XRPD pattern. In a further embodiment, Form C is characterized by a peak having a 2-Theta value from about 8.1 to about 8.5 degrees in an XRPD pattern. In a further embodiment, Form C is characterized by a peak having a 2-Theta value from about 12.2 to about 12.6 degrees in an XRPD pattern. In a further embodiment, Form C is characterized by a peak having a 2-Theta value from about 14.4 to about 14.8 degrees in an XRPD pattern. In a further embodiment, Form C is characterized by a peak having a 2-Theta value from about 17.7 to about 18.1 degrees in an XRPD pattern. In a further embodiment, Form C is characterized by a peak having a 2-Theta value from about 20.3 to about 20.7 degrees in an XRPD pattern. In a further embodiment, Form C is characterized by a peak having a 2-Theta value from about 20.7 to about 21.1 degrees in an XRPD pattern.

In another embodiment, Form C is characterized by a peak having a 2-Theta value of about 6.2 degrees in an XRPD pattern. In a further embodiment, Form C is characterized by a peak having a 2-Theta value of about 7.5 degrees in an XRPD pattern. In a further embodiment, Form C is characterized by a peak having a 2-Theta value of about 8.3 degrees in an XRPD pattern. In a further embodiment, Form C is characterized by a peak having a 2-Theta value of about 12.4 degrees in an XRPD pattern. In a further embodiment, Form C is characterized by a peak having a 2-Theta value of about 14.6 degrees in an XRPD pattern. In a further embodiment, Form C is characterized by a peak having a 2-Theta value of about 17.9 degrees in an XRPD pattern. In a further embodiment, Form C is characterized by a peak having a 2-Theta value of about 20.5 degrees in an XRPD pattern. In a further embodiment, Form C is characterized by a peak having a 2-Theta value of about 20.9 degrees in an XRPD pattern.

In another embodiment, Form C is characterized by one or more peaks in an XRPD pattern selected from about 6.2, about 7.5, about 8.3, about 12.4, about 14.6, about 17.9, about 20.5 and about 20.9 degrees as measured on a 2-Theta scale.

In still another embodiment, Form C is characterized by all of the following peaks in an XRPD pattern: about 6.2, about 7.5, about 8.3, about 12.4, about 14.6, about 17.9, about 20.5 and about 20.9 degrees as measured on a 2-Theta scale.

In another embodiment, Form C can be characterized by the X-Ray powder diffraction pattern depicted in FIG. 1. Representative peaks as observed in the XRPD pattern are provided in Table Ia below. Each peak described in Table Ia also has a corresponding peak label (A-H), which are used to describe some embodiments of the invention.

TABLE Ia

Representative XRPD peaks for Form C.

| Peak # | Angle 2-θ (°) | Peak Label |
|---|---|---|
| 1 | 6.2 | A |
| 2 | 7.5 | B |
| 3 | 8.3 | C |
| 4 | 12.4 | D |
| 5 | 14.6 | E |
| 6 | 17.9 | F |
| 7 | 20.5 | G |
| 8 | 20.9 | H |

In another embodiment, Form C can be characterized by an X-Ray powder diffraction pattern having the representative peaks listed in Table Ib.

TABLE Ib

Further representative XRPD peaks for Form C.

| Peak # | Angle 2-θ (°) |
|---|---|
| 1 | 6.2 |
| 2 | 7.5 |

TABLE Ib-continued

Further representative XRPD peaks for Form C.

| Peak # | Angle 2-θ (°) |
|---|---|
| 3 | 8.3 |
| 4 | 11.0 |
| 5 | 12.4 |
| 6 | 14.6 |
| 7 | 16.3 |
| 8 | 17.1 |
| 9 | 17.9 |
| 10 | 18.1 |
| 11 | 18.7 |
| 12 | 19.5 |
| 13 | 20.5 |
| 14 | 20.9 |
| 15 | 21.3 |
| 16 | 21.5 |
| 17 | 21.8 |
| 18 | 22.1 |
| 19 | 22.4 |
| 20 | 22.7 |

In one aspect, Compound 1 Form C can be characterized by an X-Ray powder diffraction pattern having one or more of peaks A, B, C, D, E, F, G and H as described in Table Ia.

In one embodiment of this aspect, Form C is characterized by peak A. In another embodiment, Form C is characterized by peak B. In another embodiment, Form C is characterized by peak B. In another embodiment, Form C is characterized by peak C. In another embodiment, Form C is characterized by peak D. In another embodiment, Form C is characterized by peak E. In another embodiment, Form C is characterized by peak F. In another embodiment, Form C is characterized by peak G. In another embodiment, Form C is characterized by peak H.

In another embodiment of this aspect, Form C is characterized by an X-Ray powder diffraction pattern having one of the following groups of peaks as described in Table Ia: A and B; A and C; A and D; A and E; A and F; A and G; A and H; B and C; B and D; B and E; B and F; B and G; B and H; C and D; C and E; C and F; C and G; C and H; D and E; D and F; D and G; D and H; E and F; E and G; E and H; F and G; F and H; and G and H.

In another embodiment of this aspect, Form C is characterized by an X-Ray powder diffraction pattern having one of the following groups of peaks as described in Table Ia: A, B and C; A, B and D; A, B and E; A, B and F; A, B and G; A, B and H; A, C and D; A, C and E; A, C and F; A, C and G; A, C and H; A, D and E; A, D and F; A, D and G; A, D and H; A, E and F; A, E and G; A, E and H; A, F and G; A, F and H; A, G and H; B, C and D; B, C and E; B, C and F; B, C and G; B, C and H; B, D and E; B, D and F; B, D and G; B, D and H; B, E and F; B, E and G; B, E and H; B, F and G; B, F and H; B, G and H; C, D and E; C, D F; C, D and G; C, D and H; C, E and F; C, E and G; C, E and H; C, F and G; C, F and H; C, G and H; D, E and F; D, E and G; D, E and H; D, F and G; D, F and H; D, G and H; E, F and G; E, F and H, E, G and H; and F, G and H.

In another embodiment of this aspect, Form C is characterized by an X-Ray powder diffraction pattern having one of the following groups of peaks as described in Table Ia: A, B, C and D; A, B, C and E, A, B, C and F; A, B, C and G; A, B, C and H; A, B, D and E; A, B, D and F; A, B, D and G; A, B, D and H; A, B, E and F; A, B, E and G; A, B, E and H; A, B, F and G; A, B, F and H; A, B, G and H; A, C, D and E; A, C, D and F; A, C, D and G; A, C, D and H; A, C, E and F; A, C, E and G; A, C, E and H; A, C, F and G; A, C, F and H; A, C, G and H; A, D, E and F; A, D, F and G; A, D, F and H; A, D, G and H; A, E, F and G; A, E, F and H; A, E, G and H; A, F, G and H; B, C, D and E; B, C, D and F; B, C, D and G; B, C, D and H; B, C, E and F; B, C, E and G; B, C, E and H; B, C, F and G; B, C, F and H; B, C, G and H; B, D, E and F; B, D, E and G; B, D, E and H; B, D, F and G; B, D, F and H; B, D, G and H; B, E, F and G; B, E, F and H; B, E, G and H; B, F, G and H; C, D, E and F; C, D, E and G; C, D, E and H; C, D, F and G; C, D, F and H; C, D, G and H; C, E, F and G; C, E, F and H; C, E, G and H; C, F, G and H; D, E, F and G; D, E, F and H; D, E, G and H; D, F, G and H; and E, F, G and H.

In another embodiment of this aspect, Form C is characterized by an X-Ray powder diffraction pattern having one of the following groups of peaks as described in Table Ia: A, B, C, D and E; A, B, C, D and F; A, B, C, D and G; A, B, C, D and H; A, B, C, E and F; A, B, C, E and G; A, B, C, E and H; A, B, C, F and G; A, B, C, F and H; A, B, C, G and H; A, B, C, E and F; A, B, C, E and G; A, B, C, E and H; A, B, C, F and G; A, B, C, F and H; A, B, C, G and H; A, B, D, E and F; A, B, D, E and G; A, B, D, E and H; A, B, D, F and G; A, B, D, F and H; A, B, D, G and H; A, B, E, F and G; A, B, E, F and H; A, B, E, G and H; A, B, F, G and H; A, C, D, E and F; A, C, D, E and G; A, C, D, E and H; A, C, D, F and G; A, C, D, F and H; A, C, D, G and H; A, C, E, F and G; A, C, E, F and H; A, C, E, G and H; A, C, F, G and H; A, D, E, F and G; A, D, E, F and H; A, D, E, G and H; A, D, F, G and H; A, E, F, G and H; B, C, D, E and F; B, C, D, E and G; B, C, D, E and H; B, C, D, F and G; B, C, D, F and H; B, C, D, G and H; B, C, E, F and G; B, C, E, F and H; B, C, E, G and H; B, C, F, G and H; B, D, E, F and G; B, D, E, F and H; B, D, E, G and H; B, D, F, G and H; B, E, F, G and H; C, D, E, F and G; C, D, E, F and H; C, D, E, G and H; C, D, F, G and H; C, E, F, G and H; and D, E, F, G and H.

In another embodiment of this aspect, Form C is characterized by an X-Ray powder diffraction pattern having one of the following groups of peaks as described in Table Ia: A, B, C, D, E and F; A, B, C, D, E and G; A, B, C, D, E and H; A, B, C, D, F and G; A, B, C, D, F and H; A, B, C, D, G and H; A, B, C, E, F and G; A, B, C, E, F and H; A, B, C, E, G and H; A, B, C, F, G and H; A, B, D, E, F and G; A, B, D, E, F and H; A, B, D, E, G and H; A, B, D, F, G and H; A, B, E, F, G and H; A, C, D, E, F and G; A, C, D, E, F and H; A, C, D, E, G and H; A, C, D, F, G and H; A, C, E, F, G and H; A, D, E, F, G and H; B, C, D, E, F and G; B, C, D, E, F and H; B, C, D, E, G and H; B, C, D, F, G and H; B, C, E, F, G and H; B, D, E, F, and H; and C, D, E, F, G and H.

In another embodiment of this aspect, Form C is characterized by an X-Ray powder diffraction pattern having one of the following groups of peaks as described in Table Ia: A, B, C, D, E, F and G; A, B, C, D, E, F and H; A, B, C, D, E, G and H; A, B, C, D, F, G and H; A, B, C, E, F, G and H; A, B, D, E, F, G and H; A, C, D, E, F, G and H; and B, C, D, E, F, G and H.

In another embodiment of this aspect, Form C is characterized by an X-Ray powder diffraction pattern having all of the following peaks as described in Table Ia: A, B, C, D, E, F, G and H.

In another aspect, Compound 1 Form C can be characterized by an X-Ray powder diffraction pattern having one or more of peaks that range in value within ±0.2 degrees of one or more of the peaks A, B, C, D, E, F, G and H as described in Table 1. In one embodiment of this aspect, Form C is characterized by a peak within ±0.2 degrees of A. In another embodiment, Form C is characterized by a peak within ±0.2 degrees of B. In another embodiment, Form C is characterized by a peak within ±0.2 degrees of B. In another embodiment, Form C is characterized by a peak within ±0.2 degrees of C. In another embodiment, Form C is characterized by a peak within ±0.2 degrees of D. In another embodiment, Form C is characterized by a peak within ±0.2 degrees of E. In another embodiment, Form C is characterized by a peak within ±0.2 degrees of F. In another embodiment, Form C is characterized by a peak within ±0.2 degrees of G. In another embodiment, Form C is characterized by a peak within ±0.2 degrees of H.

In another embodiment of this aspect, Form C is characterized by an X-Ray powder diffraction pattern having one of the following groups of peaks as described in Table Ia: A and B; A and C; A and D; A and E; A and F; A and G; A and H; B and C; B and D; B and E; B and F; B and G; B and H; C and D; C and E; C and F; C and G; C and H; D and E; D and F; D and G; D and H; E and F; E and G; E and H; F and G; F and H; and G and H, wherein each peak in the group is within ±0.2 degrees of the corresponding value described in Table Ia.

In another embodiment of this aspect, Form C is characterized by an X-Ray powder diffraction pattern having one of the following groups of peaks as described in Table Ia: A, B and C; A, B and D; A, B and E; A, B and F; A, B and G; A, B and H; A, C and D; A, C and E; A, C and F; A, C and G; A, C and H; A, D and E; A, D and F; A, D and G; A, D and H; A, E and F; A, E and G; A, E and H; A, F and G; A, F and H; A, G and H; B, C and D; B, C and E; B, C and F; B, C and G; B, C and H; B, D and E; B, D and F; B, D and G; B, D and H; B, E and F; B, E and G; B, E and H; B, F and G; B, F and H; B, G and H; C, D and E; C, D F; C, D and G; C, D and H; C, E and F; C, E and G; C, E and H; C, F and G; C, F and H; C, G and H; D, E and F; D, E and G; D, E and H; D, F and G; D, F and H; D, G and H; E, F and G; E, F and H, E, G and H; and F, G and H, wherein each peak in the group is within ±0.2 degrees of the corresponding value described in Table Ia.

In another embodiment of this aspect, Form C is characterized by an X-Ray powder diffraction pattern having one of the following groups of peaks as described in Table Ia: A, B, C and D; A, B, C and E, A, B, C and F; A, B, C and G; A, B, C and H; A, B, D and E; A, B, D and F; A, B, D and G; A, B, D and H; A, B, E and F; A, B, E and G; A, B, E and H; A, B, F and G; A, B, F and H; A, B, G and H; A, C, D and E; A, C, D and F; A, C, D and G; A, C, D and H; A, C, E and F; A, C, E and G; A, C, E and H; A, C, F and G; A, C, F and H; A, C, G and H; A, D, F and G; A, D, F and H; A, D, G and H; A, E, F and G; A, E, F and H; A, E, G and H; A, F, G and H; B, C, D and E; B, C, D and F; B, C, D and G; B, C, D and H; B, C, E and F; B, C, E and G; B, C, E and H; B, C, F and G; B, C, F and H; B, D, E and F; B, D, E and G; B, D, E and H; B, D, F and G; B, D, F and H; B, D, G and H; B, E, F and G; B, E, F and H; B, E, G and H; B, F, G and H; C, D, E and F; C, D, E and G; C, D, E and H; C, D, F and G; C, D, F and H; C, D, G and H; C, E, F and G; C, E, F and H; C, E, G and H; C, F, G and H; D, E, F and G; D, E, F and H; D, E, G and H; D, F, G and H; and E, F, G and H, wherein each peak in the group is within ±0.2 degrees of the corresponding value described in Table Ia.

In another embodiment of this aspect, Form C is characterized by an X-Ray powder diffraction pattern having one of the following groups of peaks as described in Table Ia: A, B, C, D and E; A, B, C, D and F; A, B, C, D and G; A, B, C, D and H; A, B, C, E and F; A, B, C, E and G; A, B, C, E and H; A, B, C, F and G; A, B, C, F and H; A, B, C, G and H; A, B, C, E and F; A, B, C, E and G; A, B, C, E and H; A, B, C, F and G; A, B, C, F and H; A, B, C, G and H; A, B, D, E and F; A, B, D, E and G; A, B, D, E and H; A, B, D, F and G; A, B, D, F and H; A, B, D, G and H; A, B, E, F and G; A, B, E, F and H; A, B, E, G and H; A, B, F, G and H; A, C, D, E and F; A, C, D, E and G; A, C, D, E and H; A, C, D, F and G; A, C, D, F and H; A, C, D, G and H; A, C, E, F and G; A, C, E, F and H; A, C, E, G and H; A, C, F, G and H; A, D, E, F and G; A, D, E, F and H; A, D, E, G and H; A, D, F, G and H; A, E, F, G and H; B, C, D, E and F; B, C, D, E and G; B, C, D, E and H; B, C, D, F and G; B, C, D, F and H; B, C, D, G and H; B, C, E, F and G; B, C, E, F and H; B, C, E, G and H; B, D, E, F, G and H; and C, D, E, F, G and H, wherein each peak in the group is within ±0.2 degrees of the corresponding value described in Table Ia.

In another embodiment of this aspect, Form C is characterized by an X-Ray powder diffraction pattern having one of the following groups of peaks as described in Table Ia: A, B, C, D, E and F; A, B, C, D, E and G; A, B, C, D, E and H; A, B, C, D, F and G; A, B, C, D, F and H; A, B, C, D, G and H; A, B, C, E, F and G; A, B, C, E, F and H; A, B, C, E, G and H; A, B, C, F, G and H; A, B, D, E, F and G; A, B, D, E, F and H; A, B, D, E, G and H; A, B, D, F, G and H; A, B, E, F, G and H; A, C, D, E, F and G; A, C, D, E, F and H; A, C, D, E, G and H; A, C, D, F, G and H; A, C, E, F, G and H; A, D, E, F, G and H; B, C, D, E, F and G; B, C, D, E, F and H; B, C, D, E, G and H; B, C, D, F, G and H; B, C, E, F, G and H; B, D, E, F, G and H; and C, D, E, F, G and H, wherein each peak in the group is within ±0.2 degrees of the corresponding value described in Table Ia.

In another embodiment of this aspect, Form C is characterized by an X-Ray powder diffraction pattern having all of the following peaks as described in Table Ia: A, B, C, D, E, F, G and H, wherein each peak in the group is within ±0.2 degrees of the corresponding value described in Table Ia.

Rietveld Refinement of Form C (Compound 1) from Powder

High resolution data were collected for a crystalline powder sample of Compound 1 Form C (Collection performed at the European Synchrotron Radiation Facility, Grenoble, France) at the beamline ID31. The X-rays are produced by three 11-mm-gap ex-vacuum undulators. The beam is monochromated by a cryogenically cooled double-crystal monochromator (Si 111 crystals). Water-cooled slits define the size of the beam incident on the monochromator, and of the monochromatic beam transmitted to the sample in the range of 0.5-2.5 mm (horizontal) by 0.1-1.5 mm (vertical). The wavelength used for the experiment was 1.29984(3) Å.

The powder diffraction data were processed and indexed using Materials Studio (Reflex module). The structure was solved using PowderSolve module of Materials Studio. The resulting solution was assessed for structural viability and subsequently refined using Rietveld refinement procedure.

The structure was solved and refined in a centrosymmetric space group $P2_1/c$ using simulated annealing algorithm. The main building block in form C is a dimer composed of two Compound 1 molecules related to each other by a crystallographic inversion center and connected via a pair of hydrogen bonds between the hydroxyl and the amide carbonyl group. These dimers are then further arranged into infinite chains and columns through hydrogen bonding, π-π stacking and van der Waals interactions. Two adjacent columns are oriented perpendicular to each other, one along the crystallographic direction a, the other along b. The columns are connected with each other through van der Waals interactions.

The 4-oxo-1H-quinoline group is locked in a nearly coplanar conformation with the amide group via an intramolecular hydrogen bond. Owing to the centrosymmetric space group, Form C structure contains two Compound 1 molecular conformations related to one another by rotation around the C1-N12 bond.

A powder pattern calculated from the crystal structure of form C and an experimental powder pattern recorded on powder diffractometer using a flat sample in reflectance mode have been compared. The peak positions are in excellent agreement. Some discrepancies in intensities of some peaks exist and are due to preferred orientation of crystallites in the flat sample.

The results of refinement, instrument setup, radiation details, lattice parameters of the resulting crystal are listed below.

TABLE IIa

Results of refinement:

| | | | |
|---|---|---|---|
| Final $R_{wp}$: | 10.24% | Final $R_p$: | 7.27% |
| Final $R_{wp}$ (without background): | 15.98% | Final CMACS: | 0.09% |

TABLE IIb

Results of further refinement:

| | | | |
|---|---|---|---|
| Final $R_{wp}$: | 10.50% | Final $R_p$: | 7.49% |
| Final $R_{wp}$ (without background): | 16.41% | Final CMACS: | 0.09% |

TABLE III

Setup

| | | | |
|---|---|---|---|
| 2θ Range (degrees): | 1.00-50.00 | Step Size (degrees): | 0.003 |
| Excluded Regions: | — | | |

TABLE IV

Radiation

| | | | |
|---|---|---|---|
| Type: | X-ray | Source: | Synchrotron |
| $\lambda_1$ (Å): | 1.299840 | Monochromator: | Double |
| Anom. Dispersion: | No | Angle: | 50.379 |
| | | Polarization: | 0.950 |

TABLE V

Lattice Parameters (Lattice Type: Monoclinic; Space Group: P2$_1$/c)

| Parameter | Value | Refined? |
|---|---|---|
| a | 12.211 Å | Yes |
| b | 5.961 Å | Yes |
| c | 32.662 Å | Yes |
| α | 90.00° | No |
| β | 119.62° | Yes |
| γ | 90.00° | No |

In one embodiment, the crystal structure of Compound 1 Form C has a monoclinic lattice type. In another embodiment, the crystal structure of Compound 1 Form C has a P2$_1$/c space group. In another embodiment, the crystal structure of Compound 1 Form C has a monoclinic lattice type and a P2$_1$/c space group.

In one embodiment, the crystal structure of Compound 1 Form C has the following unit cell dimensions:

a=12.211 Angstroms
b=5.961 Angstroms
c=32.662 Angstroms
α=90.00°
β=119.62°
γ=90.00°

Figure 2:
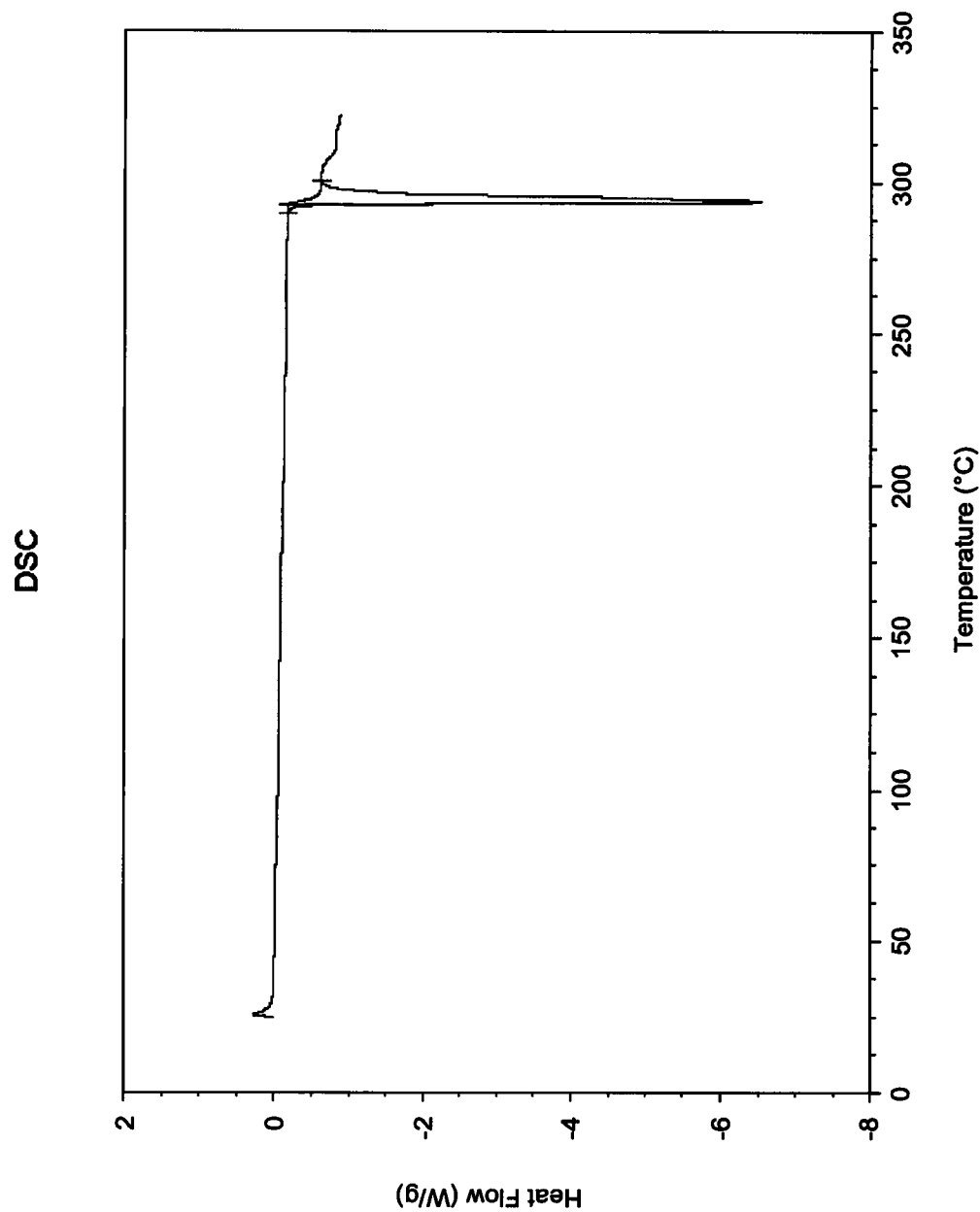
FIG. 2 is an exemplary DSC trace of Form C.
Figure 3:
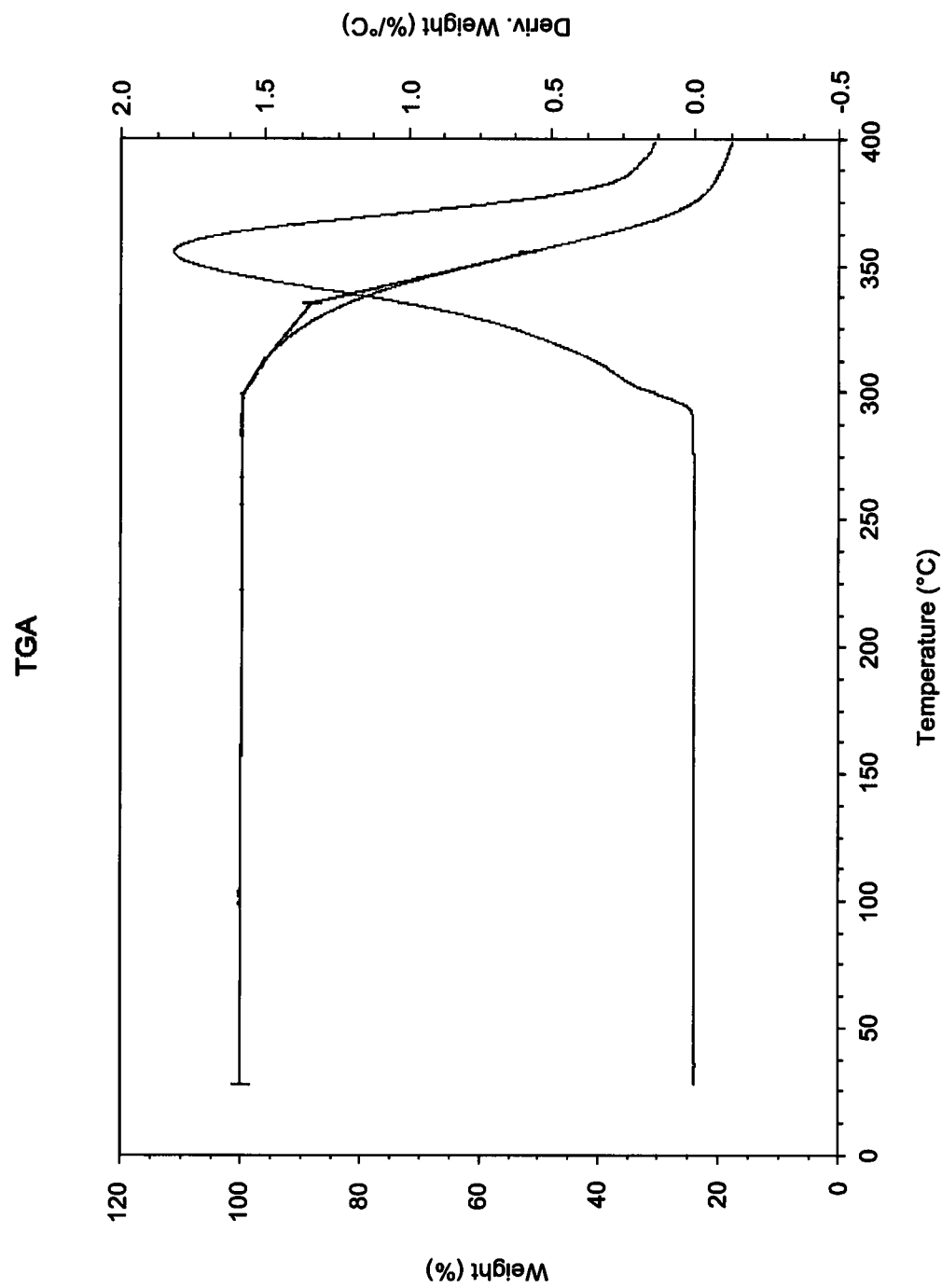
FIG. 3 is an exemplary TGA trace of Form C.

Compound 1 Form C can be characterized by an endotherm beginning at 292° C., that plateaus slightly and then peaks at 293° C. as measured by DSC (FIG. 2). Further, this endotherm preceeds an 85% weight loss, as measured by TGA (FIG. 3), which is attributed to chemical degradation.

Figure 4:
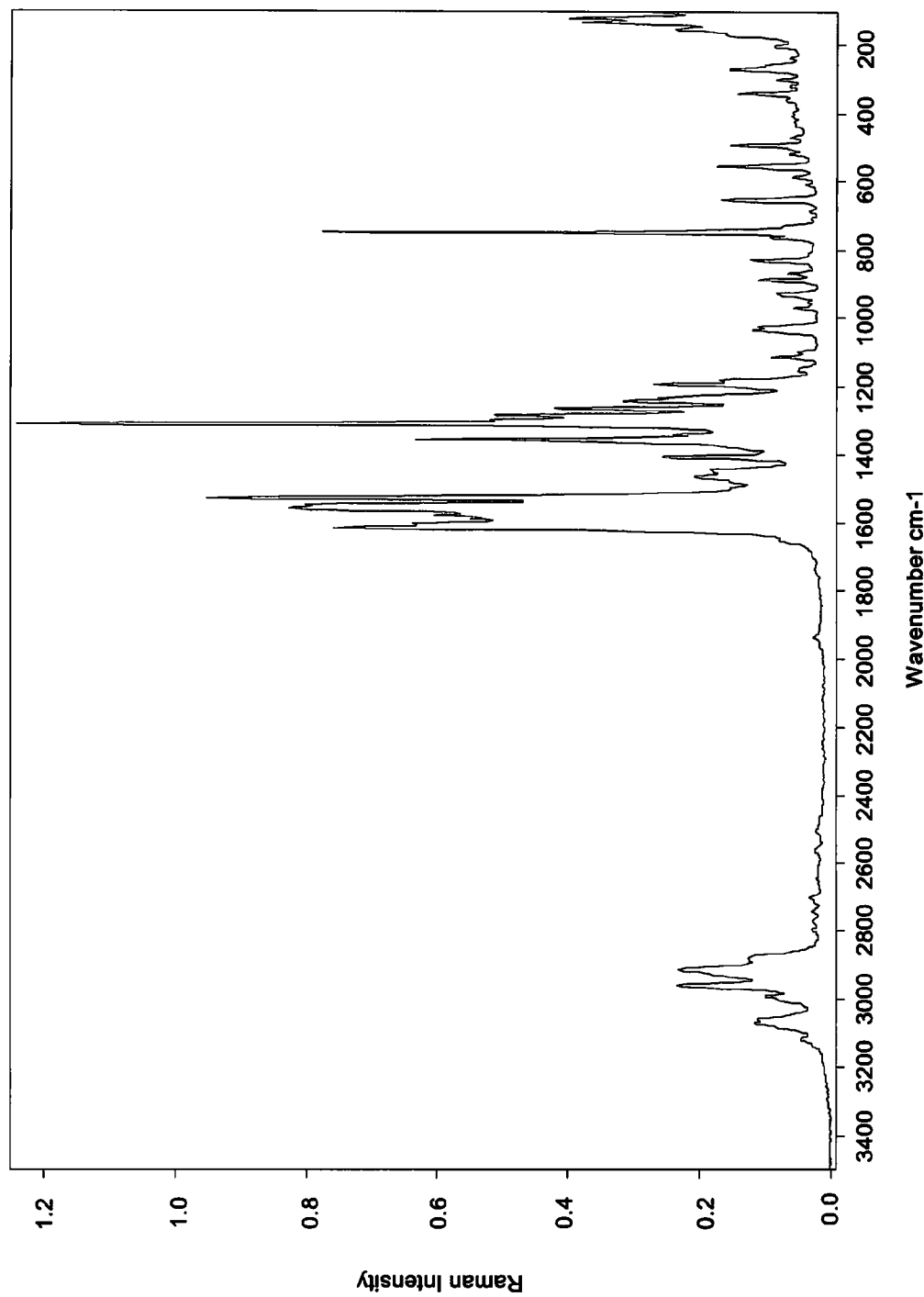
FIG. 4 is an exemplary Raman spectrum of Form C.
Figure 5:
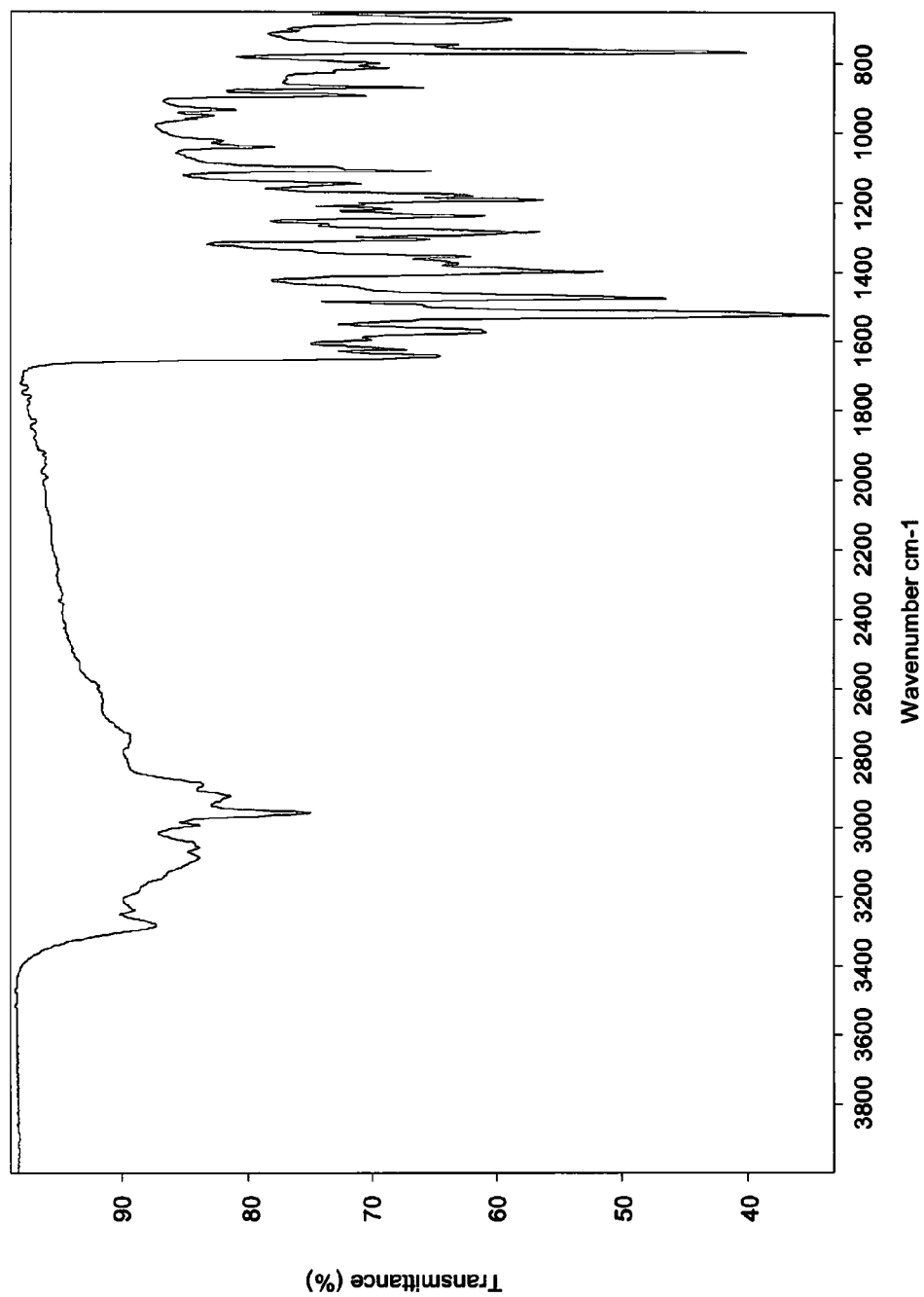
FIG. 5 is an exemplary FTIR spectrum of Form C.

Compound 1 Form C can be characterized by a FT-IR pattern as depicted in FIG. 5 and by raman spectroscopy as depicted by FIG. 4.

Figure 6:
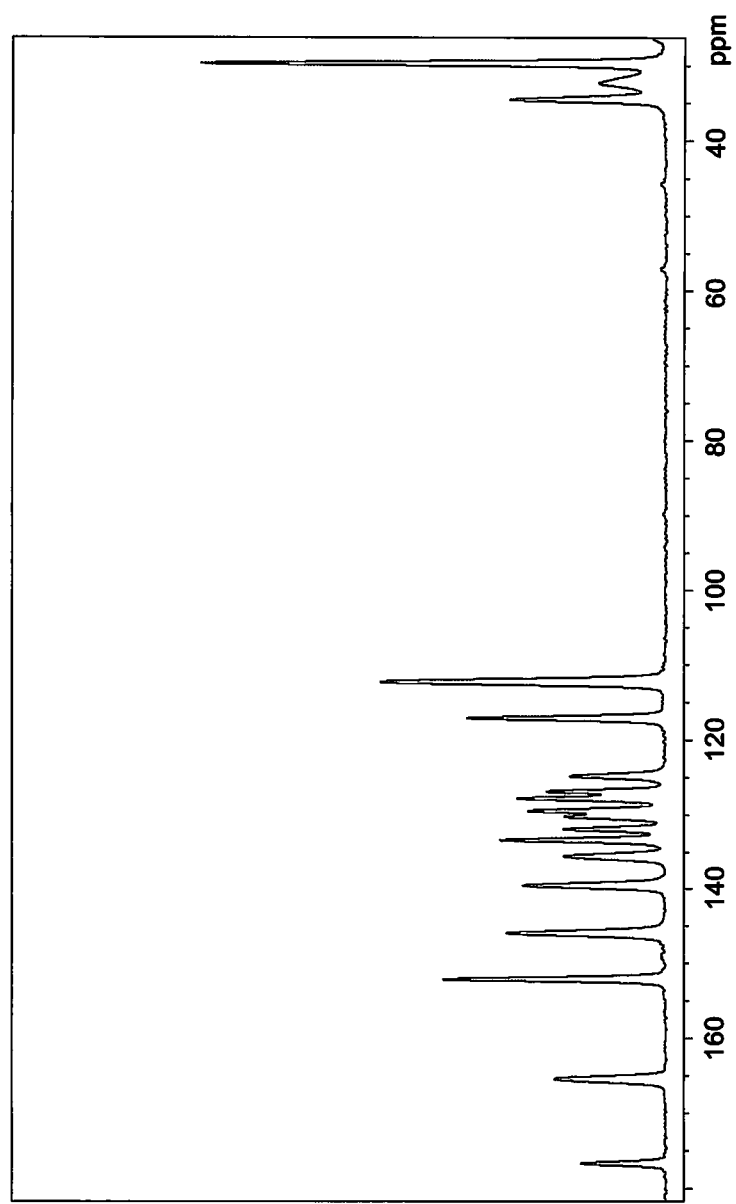
FIG. 6 is Solid State NMR Spectrum of Form C.

Compound 1 Form C can be characterize by solid state a NMR pattern as depicted in FIG. 6.

In one aspect, the invention includes Pharmaceutical compositions including Compound 1 Form C and a pharmaceutically acceptable adjuvant or carrier. In one embodiment, Compound 1 Form C can be formulated in a pharmaceutical composition, in some instances, with another therapeutic agent, for example another therapeutic agent for treating cystic fibrosis or a symptom thereof.

Processes for preparing Compound 1 Form C are exemplified herein.

Methods of treating a CFTR mediated disease, such as cystic fibrosis, in a patient include administering to said patient Compound 1 Form C or a pharmaceutical composition comprising Compound 1 Form C.

Uses, Formulation and Administration

Pharmaceutically Acceptable Compositions

In another aspect of the present invention, pharmaceutically acceptable compositions are provided, wherein these compositions comprise any of the Compounds as described herein, and optionally comprise a pharmaceutically acceptable carrier, adjuvant or vehicle. In certain embodiments, these compositions optionally further comprise one or more additional therapeutic agents.

It will also be appreciated that certain Compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a Compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the Compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a solid state form of Compound 1 described herein (e.g., Compound 1 as Form C) to a subject, preferably a mammal, in need thereof.

In yet another aspect, the present invention provides a method of treating, or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising a composition comprising a solid state form of Compound 1 described herein (e.g., Compound 1 as Form C) to a subject, preferably a mammal, in need thereof.

In another aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In some embodiments, the method includes treating or lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes treating or lessening the severity of cystic fibrosis in a patient possessing the ΔF508 mutation of human CFTR comprising administering to said patient one of the compositions as defined herein. In one embodiment, the method includes treating or lessening the severity of cystic fibrosis in a patient possessing the G551D mutation of human CFTR comprising administering to said patient one of the compositions as defined herein. In one embodiment, the method includes treating or lessening the severity of cystic fibrosis in a patient possessing the ΔF508 mutation of human CFTR on at least one allele comprising administering to said patient one of the compositions as defined herein. In one embodiment, the method includes treating or lessening the severity of cystic fibrosis in a patient possessing the ΔF508 mutation of human CFTR on both alleles comprising administering to said patient one of the compositions as defined herein. In one embodiment, the method includes treating or lessening the severity of cystic fibrosis in a patient possessing the G551D mutation of human CFTR on at least one allele comprising administering to said patient one of the compositions as defined herein. In one embodiment, the method includes treating or lessening the severity of cystic fibrosis in a patient possessing the G551D mutation of human CFTR on both alleles comprising administering to said patient one of the compositions as defined herein.

In some embodiments, the method includes lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes lessening the severity of cystic fibrosis in a patient possessing the ΔF508 mutation of human CFTR comprising administering to said patient one of the compositions as defined herein. In one embodiment, the method includes lessening the severity of cystic fibrosis in a patient possessing the G551D mutation of human CFTR comprising administering to said patient one of the compositions as defined herein. In one embodiment, the method includes lessening the severity of cystic fibrosis in a patient possessing the ΔF508 mutation of human CFTR on at least one allele comprising administering to said patient one of the compositions as defined herein. In one embodiment, the method includes lessening the severity of cystic fibrosis in a patient possessing the ΔF508 mutation of human CFTR on both alleles comprising administering to said patient one of the compositions as defined herein. In one embodiment, the method includes lessening the severity of cystic fibrosis in a patient possessing the G551D mutation of human CFTR on at least one allele comprising administering to said patient one of the compositions as defined herein. In one embodiment, the method includes lessening the severity of cystic fibrosis in a patient possessing the G551D mutation of human CFTR on both alleles comprising administering to said patient one of the compositions as defined herein.

In some aspects, the invention provides a method of treating or lessening the severity of Osteoporosis in a patient comprising administering to said patient a composition comprising a solid state form of Compound 1 described herein (e.g., Compound 1 as Form C).

In certain embodiments, the method of treating or lessening the severity of Osteoporosis in a patient comprises administering to said patient a pharmaceutical composition as described herein.

In some aspects, the invention provides a method of treating or lessening the severity of Osteopenia in a patient comprising administering to said patient a composition comprising a solid state form of Compound 1 described herein (e.g., Compound 1 as Form C).

In certain embodiments, the method of treating or lessening the severity of Osteopenia in a patient comprises administering to said patient a pharmaceutical composition as described herein.

In some aspects, the invention provides a method of bone healing and/or bone repair in a patient comprising administering to said patient a composition comprising a solid state form of Compound 1 described herein (e.g., Compound 1 as Form C).

In certain embodiments, the method of bone healing and/or bone repair in a patient comprises administering to said patient a pharmaceutical composition as described herein.

In some aspects, the invention provides a method of reducing bone resorption in a patient comprising administering to said patient a composition comprising a solid state form of Compound 1 described herein (e.g., Compound 1 as Form C).

In certain embodiments, the method of reducing bone resorption in a patient comprises administering to said patient a pharmaceutical composition as described herein.

In some aspects, the invention provides a method of increasing bone deposition in a patient comprising administering to said patient a composition comprising a solid state form of Compound 1 described herein (e.g., Compound 1 as Form C).

In certain embodiments, the method of increasing bone deposition in a patient comprises administering to said patient a pharmaceutical composition as described herein.

In some aspects, the invention provides a method of treating or lessening the severity of COPD in a patient comprising administering to said patient a composition comprising a solid state form of Compound 1 described herein (e.g., Compound 1 as Form C).

In certain embodiments, the method of treating or lessening the severity of COPD in a patient comprises administering to said patient a pharmaceutical composition as described herein.

In some aspects, the invention provides a method of treating or lessening the severity of smoke induced COPD in a patient comprising administering to said patient a composition comprising a solid state form of Compound 1 described herein (e.g., Compound 1 as Form C).

In certain embodiments, the method of treating or lessening the severity of smoke induced COPD in a patient comprises administering to said patient a pharmaceutical composition as described herein.

In some aspects, the invention provides a method of treating or lessening the severity of chronic bronchitis in a patient comprising administering to said patient a composition comprising a solid state form of Compound 1 described herein (e.g., Compound 1 as Form C).

In certain embodiments, the method of treating or lessening the severity of chronic bronchitis in a patient comprises administering to said patient a pharmaceutical composition as described herein.

According to an alternative embodiment, the present invention provides a method of treating cystic fibrosis comprising the step of administering to said mammal an effective amount of a composition comprising a compound of the present invention.

According to the invention an "effective amount" of the compound or pharmaceutically acceptable composition is that amount effective for treating or lessening the severity of one or more of the diseases, disorders or conditions as recited above.

Another aspect of the present invention provides a method of administering a pharmaceutical composition by orally administering to a patient at least once per day the composition comprising a composition comprising a solid state form of Compound 1 described herein (e.g., Compound 1 as Form C). In one embodiment, the method comprises administering a pharmaceutical composition comprising a composition comprising a solid state form of Compound 1 described herein (e.g., Compound 1 as Form C) every 24 hours. In another embodiment, the method comprises administering a pharmaceutical composition comprising a composition comprising a solid state form of Compound 1 described herein (e.g., Compound 1 as Form C) every 12 hours. In a further embodiment, the method comprises administering a composition comprising a solid state form of Compound 1 described herein (e.g., Compound 1 as Form C) three times per day. In still a further embodiment, the method comprises administering a composition comprising a solid state form of Compound 1 described herein (e.g., Compound 1 as Form C) every 4 hours.

The compounds and compositions, according to the method of the present invention, may be administered using any amount and any route of administration effective for treating or lessening the severity of one or more of the diseases, disorders or conditions as recited above.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl$^-$ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, a solid state form of Compound 1 described herein (e.g., Compound 1 as Form C) or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, a solid state form of Compound 1 described herein (e.g., Compound 1 as Form C) or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the Compound across the skin. The rate can be controlled by either providing a rate controlling membrane or by dispersing the compound in a polymer matrix or gel.

It will also be appreciated that a solid state form of Compound 1 described herein (e.g., Compound 1 as Form C) or a pharmaceutically acceptable composition thereof can be employed in combination therapies, that is Form C or a pharmaceutically acceptable composition thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S, 5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R, 4aR, 5R, 7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

A solid state form of Compound 1 described herein (e.g., Compound 1 as Form C) or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising a solid state form of Compound 1 described herein (e.g., Compound 1 as Form C) or a pharmaceutically acceptable composition thereof, and in classes and subclasses herein, and a carrier suitable for coating said implantable device. In still another aspect, the present invention includes an implantable device coated with a composition comprising a solid state form of Compound 1 described herein (e.g., Compound 1 as Form C) or a pharmaceutically acceptable composition thereof, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

In one aspect, the invention provides a kit for use in measuring the activity of CFTR or a fragment thereof in a biological sample in vitro or in vivo, comprising:
  (i) a composition comprising Compound 1 Form C;
  (ii) instructions for:
    a) contacting the composition with the biological sample; and
    b) measuring activity of said CFTR or a fragment thereof.

In one embodiment of this aspect, the kit includes instructions for:
  a) contacting an additional compound with the biological sample;
  b) measuring the activity of said CFTR or a fragment thereof in the presence of said additional compound; and
  c) comparing the activity of said CFTR or fragment thereof in the presence of said additional compound with the activity of the CFTR or fragment thereof in the presence of the composition comprising Compound 1 Form C.

In a further embodiment, the step of comparing the activity of said CFTR or fragment thereof provides a measure of the density of said CFTR or fragment thereof.

In order that the invention described herein may be more fully understood, the following examples are set forth. It should be understood that these examples are for illustrative purposes only and are not to be construed as limiting this invention in any manner.

EXAMPLES

Methods & Materials

Differential Scanning Calorimetry (DSC)

The DSC traces of Form C were obtained using TA Instruments DSC Q2000 equipped with Universal Analysis 2000 software. An amount (3-8 mg) of Compound 1 Form C was weighed into an aluminum pan and sealed with a pinhole lid. The sample was heated from 25° C. to 325° C. at 10° C./min. The sample exhibited high melting points which is consistent with highly crystalline material. In one embodiment, the melting range is about 293.3 to about 294.7° C. In a further embodiment, the melting range is about 293.8° C. to about 294.2° C. In another embodiment, the onset temperature range is about 292.2° C. to about 293.5° C. In a further embodiment, the onset temperature range is about 292.7° C. to about 293.0° C.

Thermogravimetric Analysis (TGA)

TGA was conducted on a TA Instruments model Q5000. An amount (3-5 mg) of Compound 1 Form C was placed in a platinum sample pan and heated at 10° C./min from room temperature to 400° C. Data were collected by Thermal Advantage Q Series™ software and analyzed by Universal Analysis 2000 software.

XRPD (X-Ray Powder Diffraction)

As stated previously, the XRPD patterns were acquired at room temperature in reflection mode using a Bruker D8 Advance diffractometer equipped with a sealed tube copper source and a Vantec-1 detector. The X-ray generator was operating at a voltage of 40 kV and a current of 40 mA. The data were recorded in a θ-θ scanning mode over the range of 3°-40° 2θ with a step size of 0.014° and the sample spinning at 15 rpm.

Raman and FTIR Spectroscopy

Raman spectra for Compound 1, Form C was acquired at room temperature using the VERTEX 70 FT-IR spectrometer coupled to a RAMII FT-Raman module. The sample was introduced into a clear vial, placed in the sample compartment and analyzed using the parameters outlined in the table below.

Raman Parameters

| Parameter | Setting |
| --- | --- |
| Beam splitter | CaF$_2$ |
| Laser frequency | 9395.0 cm$^{-1}$ |
| Laser power | 1000 mW |
| Save data from | 3501 to 2.94 cm$^{-1}$ |
| Resolution | 4 cm$^{-1}$ |
| Sample scan time | 64 scans |

The FTIR spectra for Compound 1, Form C was acquired at room temperature using the Bruker VERTEX 70 FT-IR spectrometer using the parameters described in the table below.

FTIR Parameters

| Parameter | Setting |
| --- | --- |
| Scan range | 4000-650 cm$^{-1}$ |
| Resolution | 4 cm$^{-1}$ |
| Scans sample | 16 |
| Scans background | 16 |
| Sampling mode | ATR, single reflection ZnSe |

TABLE VI

FTIR and Raman peak assignments for Compound 1, Form C: vs = very strong s = strong, m = medium, w = weak intensity.

| Peak assignments | FTIR Wavenumber Intensity, peak width | Raman Wavenumber Intensity, peak width |
| --- | --- | --- |
| N—H str in —C(=O)—NHR trans | 3281 m | Not observed |
| Unsaturated C—H str-substituted aromatic and olefin | 3085 m, 3056 m | 3071 w, 2991 w |
| Aliphatic C—H str | 2991 m, 2955 m, 2907 m, 2876 m | 2959 w, 2913 w, 2878 w |
| Amide C=O str + Conjugated ketone C=O str | 1643 s | Not observed |
| Olefin C=C conjugated with C=O | Not observed | 1615 s |
| Amide II in —C(=O)—NHR trans | 1524 vs | 1528 s |
| Benzene ring str | 1475 s | Not observed |
| Amide III in —C(=O)—NHR trans | 1285 s | 1310 vs |
| Aromatic C—H wag | 765 vs | Not observed |
| Aromatic in-plane bend modes | Not observed | 748 s |

SSNMR (Solid State Nuclear Magnetic Resonance Spectroscopy)

Broker-Biospin 400 MHz wide-bore spectrometer equipped with Bruker-Biospin 4 mm HFX probe was used. Samples were packed into 4 mm ZrO$_2$ rotors and spun under Magic Angle Spinning (MAS) condition with spinning speed of 12.0 kHz. The proton relaxation time was first measured using $^1$H MAS T$_1$ saturation recovery relaxation experiment in order to set up proper recycle delay of the $^{13}$C cross-polarization (CP) MAS experiment. The CP contact time of carbon CPMAS experiment was set to 2 ms. A CP proton pulse with linear ramp (from 50% to 100%) was employed. The Hartmann-Hahn match was optimized on external reference sample (glycine). TPPM15 decoupling sequence was used with the field strength of approximately 100 kHz. Some peaks from a $^{13}$C SSNMR spectrum of Compound 1 Form C are given in Table VII.

TABLE VII

Listing of some of the SSNMR peaks for Form C. Compound 1 Form C

| Peak # | Chemical Shift [ppm] | Intensity | Peak Label |
| --- | --- | --- | --- |
| 1 | 176.5 | 17.95 | A |
| 2 | 165.3 | 23.73 | B |
| 3 | 152.0 | 47.53 | C |
| 4 | 145.8 | 33.97 | D |
| 5 | 139.3 | 30.47 | E |
| 6 | 135.4 | 21.76 | F |
| 7 | 133.3 | 35.38 | G |
| 8 | 131.8 | 21.72 | H |
| 9 | 130.2 | 21.45 | I |
| 10 | 129.4 | 29.31 | J |
| 11 | 127.7 | 31.54 | K |
| 12 | 126.8 | 25.44 | L |
| 13 | 124.8 | 20.47 | M |
| 14 | 117.0 | 42.4 | N |
| 15 | 112.2 | 61.08 | O |
| 16 | 34.5 | 33.34 | P |
| 17 | 32.3 | 14.42 | Q |
| 18 | 29.6 | 100 | R |

In some embodiments, the $^{13}$C SSNMR spectrum of Compound 1 Form C is includes one or more of the following peaks: 176.5 ppm, 165.3 ppm, 152.0 ppm, 145.8 ppm, 139.3 ppm, 135.4 ppm, 133.3 ppm, 131.8 ppm, 130.2 ppm, 129.4 ppm, 127.7 ppm, 126.8 ppm, 124.8 ppm, 117.0 ppm, 112.2 ppm, 34.5 ppm, 32.3 ppm and 29.6 ppm.

In some embodiments, the $^{13}$C SSNMR spectrum of Compound 1 Form C includes all of the following peaks: 152.0 ppm, 135.4 ppm, 131.8 ppm, 130.2 ppm, 124.8 ppm, 117.0 ppm and 34.5 ppm.

In some embodiments, the $^{13}$C SSNMR spectrum of Compound 1 Form C includes all of the following peaks: 152.0 ppm, 135.4 ppm, 131.8 ppm and 117.0 ppm.

In some embodiments, the $^{13}$C SSNMR spectrum of Compound 1 Form C includes all of the following peaks: 135.4 ppm and 131.8 ppm.

In some embodiments, the SSNMR of Compound 1 Form C includes a peak at about 152.0 ppm, about 135.4, about 131.8 ppm, and about 117 ppm.

In one aspect, the invention includes Compound 1 Form C which is characterized by a $^{13}$C SSNMR spectrum having one or more of the following peaks: C, F, H, I, M, N and P, as described by Table VII.

In one embodiment of this aspect, Form C is characterized by one peak in a $^{13}$C SSNMR spectrum, wherein the peak is selected from C, F, H, I, M, N and P, as described by Table VII.

In another embodiment of this aspect, Form C is characterized by a $^{13}$C SSNMR spectrum having a group of peaks selected from C and F; C and H; C and N; F and H; F and N; and H and N, as described by Table VII. In a further embodiment, the $^{13}$C SSNMR spectrum includes the peaks I, M and P as described by Table VII.

In another embodiment of this aspect, Form C is characterized by a $^{13}$C SSNMR spectrum having a group of peaks selected from C, F and H; C, H and N; and F, H and N, as described by Table VII. In a further embodiment, the $^{13}$C SSNMR spectrum includes the peaks I, M and P as described by Table VII.

In another embodiment of this aspect, Form C is characterized by a $^{13}$C SSNMR spectrum having the following group of peaks: C, F, H and N, as described by Table VII. In a further embodiment, the $^{13}$C SSNMR spectrum includes the peaks I, M and P as described by Table VII.

In another embodiment of this aspect, Form C is characterized by a $^{13}$C SSNMR spectrum having a group of peaks selected from C and F; C and H, C and N; C and I; C and M; or C and P, as described by Table VII. In another embodiment of this aspect, Form C is characterized by a $^{13}$C SSNMR spectrum having a group of peaks selected from F and H; F and N; F and I; F and M; or F and P as described by Table VII. In another embodiment of this aspect, Form C is characterized by a $^{13}$C SSNMR spectrum having a group of peaks selected from H and N; H and I; H and M; or H and P as described by Table VII. In another embodiment of this aspect, Form C is characterized by a $^{13}$C SSNMR spectrum having a group of peaks selected from N and I; N and M; or N and P as described by Table VII. In another embodiment of this aspect, Form C is characterized by a $^{13}$C SSNMR spectrum having a group of peaks selected from I and M; I and P or M and P as described by Table VII.

In another embodiment of this aspect, Form C is characterized by a $^{13}$C SSNMR spectrum having a group of peaks selected from C, F and H; C, F and N; C, F and I; C, F and M; or C, F and P as described by Table VII. In another embodiment of this aspect, Form C is characterized by a $^{13}$C SSNMR spectrum having a group of peaks selected from C, H and N; C, H and I; C, H and M; or C, H and P as described by Table VII. In another embodiment of this aspect, Form C is characterized by a $^{13}$C SSNMR spectrum having a group of peaks selected from C, N and I; C, N and M; or C, N and P as described by Table VII. In another embodiment of this aspect, Form C is characterized by a $^{13}$C SSNMR spectrum having a group of peaks selected from C, I and M; or C, I and P as described by Table VII. In another embodiment of this aspect, Form C is characterized by a $^{13}$C SSNMR spectrum having a group of peaks selected from C, M and P as described by Table VII. In another embodiment of this aspect, Form C is characterized by a $^{13}$C SSNMR spectrum having a group of peaks selected from F, H, and N; F, H and I; F, H and M; or F, H and P as described by Table VII. In another embodiment of this aspect, Form C is characterized by a $^{13}$C SSNMR spectrum having a group of peaks selected from F, N and I; F, N and M; or F, N and P as described by Table VII. In another embodiment of this aspect, Form C is characterized by a $^{13}$C SSNMR spectrum having a group of peaks selected from F, I and M; or F, I and P as described by Table VII. In another embodiment of this aspect, Form C is characterized by a $^{13}$C SSNMR spectrum having a group of peaks selected from F, M and P as described by Table VII. In another embodiment of this aspect, Form C is characterized by a $^{13}$C SSNMR spectrum having a group of peaks selected from H, N and I; H, N and M; or H, N and P as described by Table VII. In another embodiment of this aspect, Form C is characterized by a $^{13}$C SSNMR spectrum having a group of peaks selected from H, I and M; or H, I and P as described by Table VII. In another embodiment of this aspect, Form C is characterized by a $^{13}$C SSNMR spectrum having a group of peaks selected from H, M and P as described by Table VII. In another embodiment of this aspect, Form C is characterized by a $^{13}$C SSNMR spectrum having a group of peaks selected from N, I and M; or N, I and P as described by Table VII. In another embodiment of this aspect, Form C is characterized by a $^{13}$C SSNMR spectrum having a group of peaks selected from N, M and P as described by Table VII. In another embodiment of this aspect, Form C is characterized by a $^{13}$C SSNMR spectrum having a group of peaks selected from I, M and P as described by Table VII.

In another embodiment of this aspect, Form C is characterized by a $^{13}$C SSNMR spectrum having a group of peaks selected from C, F, H, and N; C, F H, and I; C, F H, and M; or C, F H, and P as described by Table VII. In another embodiment of this aspect, Form C is characterized by a $^{13}$C SSNMR spectrum having a group of peaks selected from F, H, N and I; F, H, N and M; or F, H, N and P as described by Table VII. In another embodiment of this aspect, Form C is characterized by a $^{13}$C SSNMR spectrum having a group of peaks selected from H, N, I and M; H, N, I and P; or H, N, I and C as described by Table VII. In another embodiment of this aspect, Form C is characterized by a $^{13}$C SSNMR spectrum having a group of peaks selected from N, I, M and P; N, I, M and C; or N, I, M and F as described by Table VII. In another embodiment of this aspect, Form C is characterized by a $^{13}$C SSNMR spectrum having a group of peaks selected from I, M, P and C; I, M, P and F; I, M, P and H as described by Table VII.

In another embodiment of this aspect, Form C is characterized by a $^{13}$C SSNMR spectrum having a group of peaks selected from C, H, N and I; C, H, N, and M; or C, H, N, and P as described by Table VII. In another embodiment of this aspect, Form C is characterized by a $^{13}$C SSNMR spectrum having a group of peaks selected from C, N, I and M; C, N, I and P; or C, N, I and F as described by Table VII. In another embodiment of this aspect, Form C is characterized by a $^{13}$C SSNMR spectrum having a group of peaks selected from C, I, M and P; C, I, M and F; or C, I, M and H as described by Table VII. In another embodiment of this aspect, Form C is characterized by a $^{13}$C SSNMR spectrum having a group of peaks selected from C, M, P and F; C, M, P and H; or C, M, P and N as described by Table VII. In another embodiment of this aspect, Form C is characterized by a $^{13}$C SSNMR spectrum having a group of peaks selected from F, N, I and M; F, N, I and P; or F, N, I and C as described by Table VII. In another embodiment of this aspect, Form C is characterized by a $^{13}$C SSNMR spectrum having a group of peaks selected from F, I, M and P; F, I, M and C; F, I, M and H; or F, I, M and N as described by Table VII. In another embodiment of this aspect, Form C is characterized by a $^{13}$C SSNMR spectrum having a group of peaks selected from F, M, P and C; F, M, P and H; or F, M, P and N as described by Table VII. In another embodiment of this aspect, Form C is characterized by a $^{13}$C SSNMR spectrum having a group of peaks selected from H, I, M and P; H, I, M and C; or H, I, M and F as described by Table VII. In another embodiment of this aspect, Form C is characterized by a $^{13}$C SSNMR spectrum having a group of peaks selected from N, M, P and C; N, M, P and F; or N, M, P and H as described by Table VII. In another embodiment of this aspect, Form C is characterized by a $^{13}$C SSNMR spectrum having a group of peaks selected from N, M, C and F; or N, M, C and H as described by Table VII. In another embodiment of this aspect, Form C is characterized by a $^{13}$C SSNMR spectrum having a group of peaks selected from N, M, F and P as described by Table VII. In another embodiment of this aspect, Form C is characterized by a $^{13}$C SSNMR spectrum having a group of peaks selected from N, M, H and P as described by Table VII. In another embodiment of this aspect, Form C is characterized by a $^{13}$C SSNMR spectrum having a group of peaks selected from C, H, I and P; C, F, I and P; C, F, N and P or F, H, I and P as described by Table VII.

In another embodiment of this aspect, Form C is characterized by a $^{13}$C SSNMR spectrum having a group of peaks selected from C, F, H, N and I; C, F, H, N and M; or C, F, H, N and P; C, F, H, I and M; C, F, H, I and P; C, F, H, M and P; C, F, N, I and M; C, F, N, I and P; C, F, N, M and P; C, H, N, I and M; C, H, N, I and P; C, H, N, M and P; C, H, I, M and P; F, H, N, I and M; F, H, N, I and P; F, H, N, M and P; F, H, I, M and P; F, N, I, M and P or H, N, I, M and P as described by Table VII.

In another embodiment of this aspect, Form C is characterized by a $^{13}$C SSNMR spectrum having a group of peaks selected from C, F, H, N and I; C, F, H, N and M; or C, F, H, N and P as described by Table VII. In another embodiment of this aspect, Form C is characterized by a $^{13}$C SSNMR spectrum having a group of peaks selected from C, H, N, I and M; or C, H, N, I and P as described by Table VII. In another embodiment of this aspect, Form C is characterized by a $^{13}$C SSNMR spectrum having a group of peaks selected from C, N, I, M and P; or C, N, I, M and F as described by Table VII. In another embodiment of this aspect, Form C is characterized by a $^{13}$C SSNMR spectrum having a group of peaks selected from C, I, M, P and F; or C, I, M, P and H as described by Table VII. In another embodiment of this aspect, Form C is characterized by a $^{13}$C SSNMR spectrum having a group of peaks selected from C, M, P, F and H; or C, M, P, F and N as described by Table VII. In another embodiment of this aspect, Form C is characterized by a $^{13}$C SSNMR spectrum having a group of peaks selected from C, P, F, H and I; or C, P, F, H and M as described by Table VII. In another embodiment of this aspect, Form C is characterized by a $^{13}$C SSNMR spectrum having a group of peaks selected from F, H, N, I and M; or F, H, N, I and P as described by Table VII. In another embodiment of this aspect, Form C is characterized by a $^{13}$C SSNMR spectrum having a group of peaks selected from F, N, I, M and P; or F, N, I, M and C as described by Table VII. In another embodiment of this aspect, Form C is characterized by a $^{13}$C SSNMR spectrum having a group of peaks selected from F, I, M, C and H; F, I, M, C and N as described by Table VII. In another embodiment of this aspect, Form C is characterized by a $^{13}$C SSNMR spectrum having a group of peaks selected from F, M, P, C and H; F, M, P, C and N, N, I and M; or F, H, N, I and P as described by Table VII. In another embodiment of this aspect, Form C is characterized by a $^{13}$C SSNMR spectrum having a group of peaks selected from H, N, I M, and P as described by Table VII. In another embodiment of this aspect, Form C is characterized by a $^{13}$C SSNMR spectrum having a group of peaks selected from H, I M, P and F as described by Table VII. In another embodiment of this aspect, Form C is characterized by a $^{13}$C SSNMR spectrum having a group of peaks selected from H, M, P, C and F as described by Table VII. In another embodiment of this aspect, Form C is characterized by a $^{13}$C SSNMR spectrum having a group of peaks selected from H, P, C, F and I as described by Table VII.

In another embodiment of this aspect, Form C is characterized by a $^{13}$C SSNMR spectrum having a group of peaks selected from C, F, H, N, I, and M; or C, F, H, N, I and P as described by Table VII. In another embodiment of this aspect, Form C is characterized by a $^{13}$C SSNMR spectrum having a group of peaks selected from F, H, N, I, M and P as described by Table VII. In another embodiment of this aspect, Form C is characterized by a $^{13}$C SSNMR spectrum having a group of peaks selected from H, N, I, M, P and C as described by Table VII. In another embodiment of this aspect, Form C is characterized by a $^{13}$C SSNMR spectrum having a group of peaks selected from N, I, M, P, C and F as described by Table VII. In another embodiment of this aspect, Form C is characterized by a $^{13}$C SSNMR spectrum having a group of peaks selected from M, P, C, F, H and N as described by Table VII.

In another embodiment of this aspect, Form C is characterized by a $^{13}$C SSNMR spectrum having a group of peaks selected from C, F, H, N, I, and M; C, F, H, N, I and P; C, F, H, N, M and P; C, F, H, I, M and P; C, F, N, I, M and P; C, H, N, I, M and P or F, H, N, I, M and P as described by Table VII.

In another embodiment of this aspect, Form C is characterized by a $^{13}$C SSNMR spectrum having a group of peaks selected from C, F, H, N, I, M and P as described by Table VII.

SYNTHETIC EXAMPLES

Example 1

Total Synthesis of
4-oxo-1,4-dihydroquinoline-3-carboxylic acid (26)

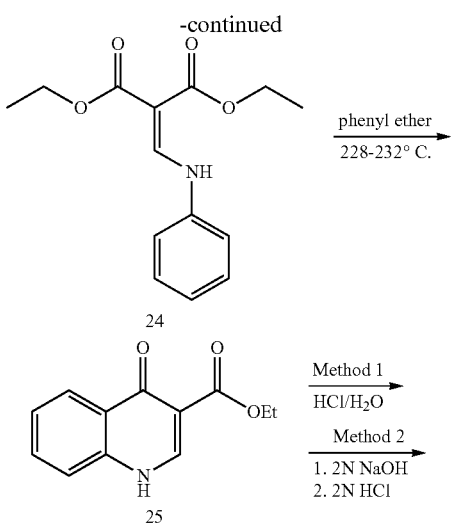

Procedure for the Preparation of ethyl 4-oxo-1,4-dihydroquinoline-3-carboxylate (25)

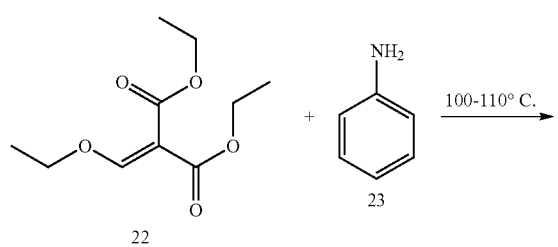

Compound 23 (4.77 g, 47.7 mmol) was added dropwise to compound 22 (10 g, 46.3 mmol) with subsurface $N_2$ flow to drive out ethanol below 30° C. for 0.5 hours. The solution was then heated to 100-110° C. and stirred for 2.5 hours. After cooling the mixture to below 60° C., diphenyl ether was added. The resulting solution was added dropwise to diphenyl ether that had been heated to 228-232° C. for 1.5 hours with subsurface $N_2$ flow to drive out ethanol. The mixture was stirred at 228-232° C. for another 2 hours, cooled to below 100° C. and then heptane was added to precipitate the product. The resulting slurry was stirred at 30° C. for 0.5 hours. The solids were then filtrated, and the cake was washed with heptane and dried in vacuo to give compound 25 as brown solid. $^1$H NMR (DMSO-$d_6$; 400 MHz) δ 12.25 (s), δ 8.49 (d), δ 8.10 (m), δ 7.64 (m), δ 7.55 (m), δ 7.34 (m), δ 4.16 (q), δ 1.23 (t).

Procedure for the Preparation of 4-oxo-1,4-dihydroquinoline-3-carboxylic acid (26)

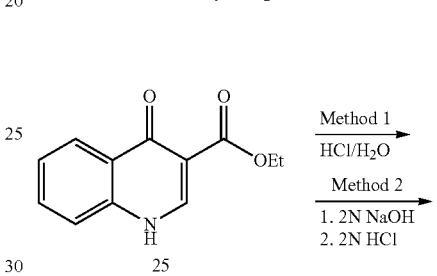

Method 1

Compound 25 (1.0 eq) was suspended in a solution of HCl (10.0 eq) and $H_2O$ (11.6 vol). The slurry was heated to 85-90° C., although alternative temperatures are also suitable for this hydrolysis step. For example, the hydrolysis can alternatively be performed at a temperature of from about 75 to about 100° C. In some instances, the hydrolysis is performed at a temperature of from about 80 to about 95° C. In others, the hydrolysis step is performed at a temperature of from about 82 to about 93° C. (e.g., from about 82.5 to about 92.5° C. or from about 86 to about 89° C.). After stirring at 85-90° C. for approximately 6.5 hours, the reaction was sampled for reaction completion. Stirring may be performed under any of the temperatures suited for the hydrolysis. The solution was then cooled to 20-25° C. and filtered. The reactor/cake was rinsed with $H_2O$ (2 vol×2). The cake was then washed with 2 vol $H_2O$ until the pH≥3.0. The cake was then dried under vacuum at 60° C. to give compound 26.

Method 2

Compound 25 (11.3 g, 52 mmol) was added to a mixture of 10% NaOH (aq) (10 mL) and ethanol (100 mL). The solution was heated to reflux for 16 hours, cooled to 20-25° C. and then the pH was adjusted to 2-3 with 8% HCl. The mixture was then stirred for 0.5 hours and filtered. The cake was washed with water (50 mL) and then dried in vacuo to give compound 26 as a brown solid. $^1$H NMR (DMSO-$d_6$; 400 MHz) δ 15.33 (s), δ 13.39 (s), δ 8.87 (s), δ 8.26 (m), δ 7.87 (m), δ 7.80 (m), δ 7.56 (m).

Example 2

Total Synthesis of N-(2,4-di-tert-butyl-5-hydroxyphenyl)-4-oxo-1,4-dihydroquinoline-3-carboxamide (1)

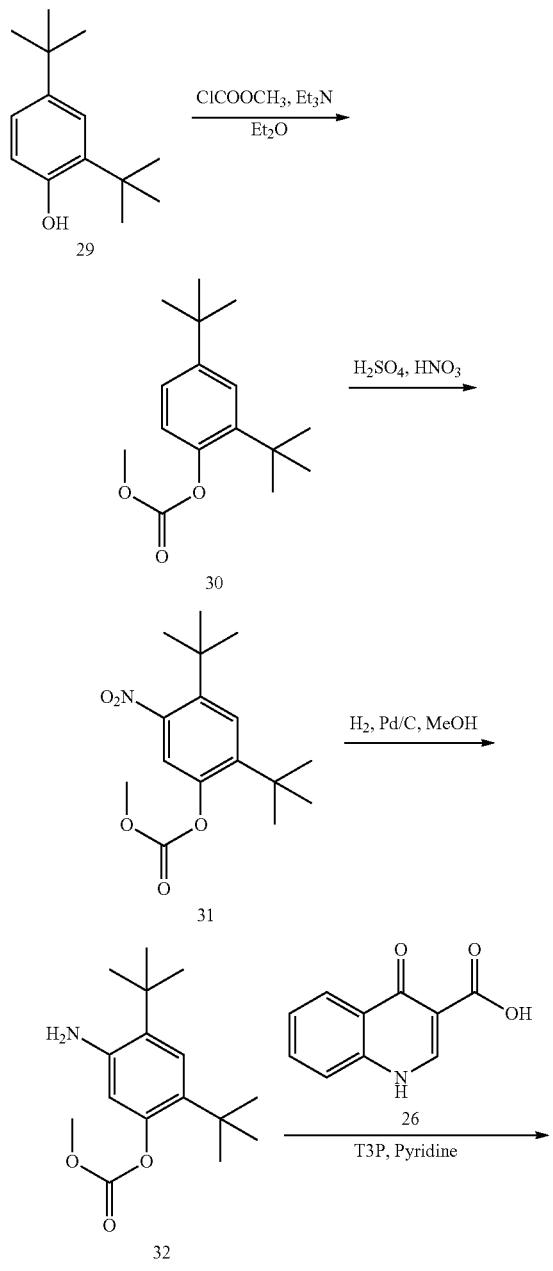

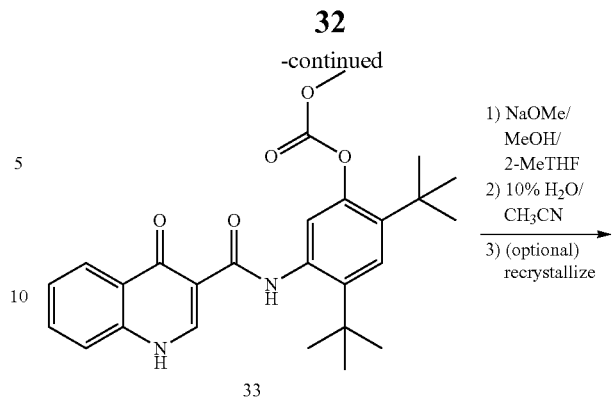

Procedure for the Preparation of 2,4-di-tert-butylphenyl methyl carbonate (30)

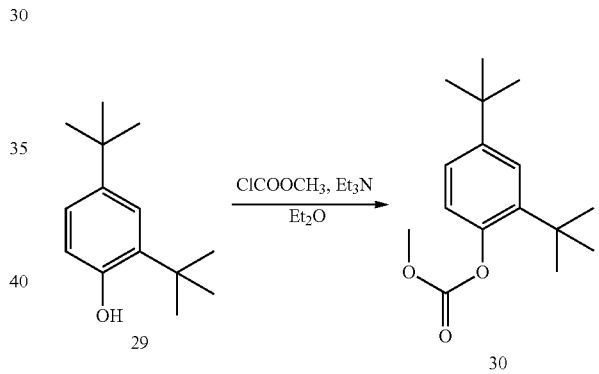

Method 1

To a solution of 2,4-di-tert-butyl phenol, 29, (10 g, 48.5 mmol) in diethyl ether (100 mL) and triethylamine (10.1 mL, 72.8 mmol), was added methyl chloroformate (7.46 mL, 97 mmol) dropwise at 0° C. The mixture was then allowed to warm to room temperature and stir for an additional 2 hours. An additional 5 mL triethylamine and 3.7 mL methyl chloroformate was then added and the reaction stirred overnight. The reaction was then filtered, the filtrate was cooled to 0° C., and an additional 5 mL triethylamine and 3.7 mL methyl chloroformate was then added and the reaction was allowed to warm to room temperature and then stir for an addition 1 hours. At this stage, the reaction was almost complete and was worked up by filtering, then washing with water (2×), followed by brine. The solution was then concentrated to produce a yellow oil and purified using column chromatography to give compound 30. $^1$H NMR (400 MHz, DMSO-$d_6$) δ 7.35 (d, J=2.4 Hz, 1H), 7.29 (dd, J=8.4, 2.4 Hz, 1H), 7.06 (d, J=8.4 Hz, 1H), 3.85 (s, 3H), 1.30 (s, 9H), 1.29 (s, 9H).

Method 2

To a reactor vessel charged with 4-dimethylaminopyridine (DMAP, 3.16 g, 25.7 mmol) and 2,4-ditert-butyl phenol (compound 29, 103.5 g, 501.6 mmol) was added methylene chloride (415 g, 313 mL) and the solution was agitated until all solids dissolved. Triethylamine (76 g, 751 mmol) was then added and the solution was cooled to 0-5° C. Methyl chloroformate (52 g, 550.3 mmol) was then added dropwise over 2.5-4 hours, while keeping the solution temperature between 0-5° C. The reaction mixture was then slowly heated to 23-28° C. and stirred for 20 hours. The reaction was then cooled to 10-15° C. and charged with 150 mL water. The mixture was stirred at 15-20° C. for 35-45 minutes and the aqueous layer was then separated and extracted with 150 mL methylene chloride. The organic layers were combined and neutralized with 2.5% HCl (aq) at a temperature of 5-20° C. to give a final pH of 5-6. The organic layer was then washed with water and concentrated in vacuo at a temperature below 20° C. to 150 mL to give compound 30 in methylene chloride.

Procedure for the Preparation of
5-nitro-2,4-di-tert-butylphenyl methyl carbonate (31)

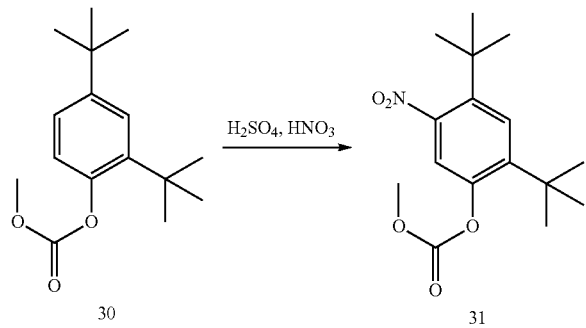 [SMILES: COC(=O)Oc1ccc(C(C)(C)C)cc1C(C)(C)C ; COC(=O)Oc1cc([N+](=O)[O-])c(C(C)(C)C)cc1C(C)(C)C]

Method 1

To a stirred solution of compound 30 (6.77 g, 25.6 mmol) was added 6 mL of a 1:1 mixture of sulfuric acid and nitric acid at 0° C. dropwise. The mixture was allowed to warm to room temperature and stirred for 1 hour. The product was purified using liquid chromatography (ISCO, 120 g, 0-7% EtOAc/Hexanes, 38 min) producing about an 8:1-10:1 mixture of regioisomers of compound 31 as a white solid. $^1$H NMR (400 MHz, DMSO-$d_6$) δ 7.63 (s, 1H), 7.56 (s, 1H), 3.87 (s, 3H), 1.36 (s, 9H), 1.32 (s, 9H). HPLC ret. time 3.92 min 10-99% CH$_3$CN, 5 min run; ESI-MS 310 m/z (MH)$^+$.

Method 2

To compound 30 (100 g, 378 mmol) was added DCM (540 g, 408 mL). The mixture was stirred until all solids dissolved, and then cooled to −5-0° C. Concentrated sulfuric acid (163 g) was then added dropwise, while maintaining the initial temperature of the reaction, and the mixture was stirred for 4.5 hours. Nitric acid (62 g) was then added dropwise over 2-4 hours while maintaining the initial temperature of the reaction, and was then stirred at this temperature for an additional 4.5 hours. The reaction mixture was then slowly added to cold water, maintaining a temperature below 5° C. The quenched reaction was then heated to 25° C. and the aqueous layer was removed and extracted with methylene chloride. The combined organic layers were washed with water, dried using Na$_2$SO$_4$, and concentrated to 124-155 mL. Hexane (48 g) was added and the resulting mixture was again concentrated to 124-155 mL. More hexane (160 g) was subsequently added to the mixture. The mixture was then stirred at 23-27° C. for 15.5 hours, and was then filtered. To the filter cake was added hexane (115 g), the resulting mixture was heated to reflux and stirred for 2-2.5 hours. The mixture was then cooled to 3-7° C., stirred for an additional 1-1.5 hours, and filtered to give compound 31 as a pale yellow solid.

Procedure for the Preparation of
5-amino-2,4-di-tert-butylphenyl methyl carbonate (32)

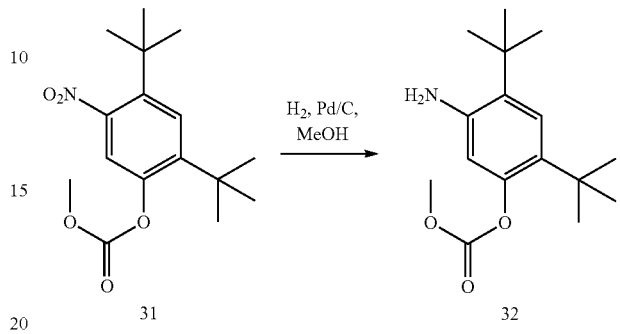

2,4-Di-tert-butyl-5-nitrophenyl methyl carbonate (1.00 eq) was charged to a suitable hydrogenation reactor, followed by 5% Pd/C (2.50 wt % dry basis, Johnson-Matthey Type 37). MeOH (15.0 vol) was charged to the reactor, and the system was closed. The system was purged with N$_2$ (g), and was then pressurized to 2.0 Bar with H$_2$ (g). The reaction was performed at a reaction temperature of 25° C.+/−5° C. When complete, the reaction was filtered, and the reactor/cake was washed with MeOH (4.00 vol). The resulting filtrate was distilled under vacuum at no more than 50° C. to 8.00 vol. Water (2.00 vol) was added at 45° C.+/−5° C. The resultant slurry was cooled to 0° C.+/−5. The slurry was held at 0° C.+/−5° C. for no less than 1 hour, and filtered. The cake was washed once with 0° C.+/−5° C. MeOH/H$_2$O (8:2) (2.00 vol). The cake was dried under vacuum (−0.90 bar and −0.86 bar) at 35° C.-40° C. to give compound 32. $^1$H NMR (400 MHz, DMSO-$d_6$) δ 7.05 (s, 1H), 6.39 (s, 1H), 4.80 (s, 2H), 3.82 (s, 3H), 1.33 (s, 9H), 1.23 (s, 9H).

Once the reaction was complete, the resulting mixture was diluted with from about 5 to 10 volumes of MeOH (e.g., from about 6 to about 9 volumes of MeOH, from about 7 to about 8.5 volumes of MeOH, from about 7.5 to about 8 volumes of MeOH, or about 7.7 volumes of MeOH, heated to a temperature of about 35±5° C., filtered, washed, and dried, as described above.

Preparation of N-(2,4-di-tert-butyl-5-hydroxyphenyl)-4-oxo-1,4-dihydroquinoline-3-carboxamide (1)

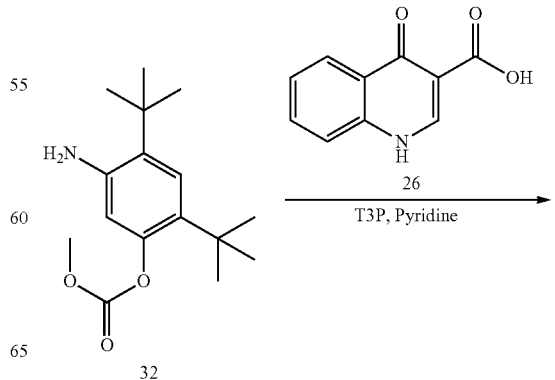

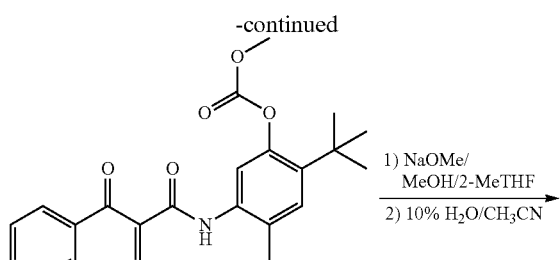

4-Oxo-1,4-dihydroquinoline-3-carboxylic acid, 26, (1.0 eq) and 5-amino-2,4-di-tert-butylphenyl methyl carbonate, 32, (1.1 eq) were charged to a reactor. 2-MeTHF (4.0 vol, relative to the acid) was added followed by T3P® 50% solution in 2-MeTHF (1.7 eq). The T3P charged vessel was washed with 2-MeTHF (0.6 vol). Pyridine (2.0 eq) was then added, and the resulting suspension was heated to 47.5+/−5.0° C. and held at this temperature for 8 hours. A sample was taken and checked for completion by HPLC. Once complete, the resulting mixture was cooled to 25.0° C.+/−2.5° C. 2-MeTHF was added (12.5 vol) to dilute the mixture. The reaction mixture was washed with water (10.0 vol) 2 times. 2-MeTHF was added to bring the total volume of reaction to 40.0 vol (~16.5 vol charged). To this solution was added NaOMe/MeOH (1.7 equiv) to perform the methanolysis. The reaction was stirred for no less than 1.0 hour, and checked for completion by HPLC. Once complete, the reaction was quenched with 1 N HCl (10.0 vol), and washed with 0.1 N HCl (10.0 vol). The organic solution was polish filtered to remove any particulates and placed in a second reactor. The filtered solution was concentrated at no more than 35° C. (jacket temperature) and no less than 8.0° C. (internal reaction temperature) under reduced pressure to 20 vol. CH$_3$CN was added to 40 vol and the solution concentrated at no more than 35° C. (jacket temperature) and no less than 8.0° C. (internal reaction temperature) to 20 vol. The addition of CH$_3$CN and concentration cycle was repeated 2 more times for a total of 3 additions of CH$_3$CN and 4 concentrations to 20 vol. After the final concentration to 20 vol, 16.0 vol of CH$_3$CN was added followed by 4.0 vol of H$_2$O to make a final concentration of 40 vol of 10% H$_2$O/CH$_3$CN relative to the starting acid. This slurry was heated to 78.0° C.+/−5.0° C. (reflux). The slurry was then stirred for no less than 5 hours. The slurry was cooled to 0.0° C.+/−5° C. over 5 hours, and filtered. The cake was washed with 0.0° C.+/−5.0° C. CH$_3$CN (5 vol) 4 times. The resulting solid (compound 1) was dried in a vacuum oven at 50.0° C.+/−5.0° C. $^1$H NMR (400 MHz, DMSO-d$_6$) δ 12.8 (s, 1H), 11.8 (s, 1H), 9.2 (s, 1H), 8.9 (s, 1H), 8.3 (s, 1H), 7.2 (s, 1H), 7.9 (t, 1H), 7.8 (d, 1H), 7.5 (t, 1H), 7.1 (s, 1H), 1.4 (s, 9H), 1.4 (s, 9H).

Alternative Preparation of N-(2,4-di-tert-butyl-5-hydroxyphenyl)-4-oxo-1,4-dihydroquinoline-3-carboxamide (1)

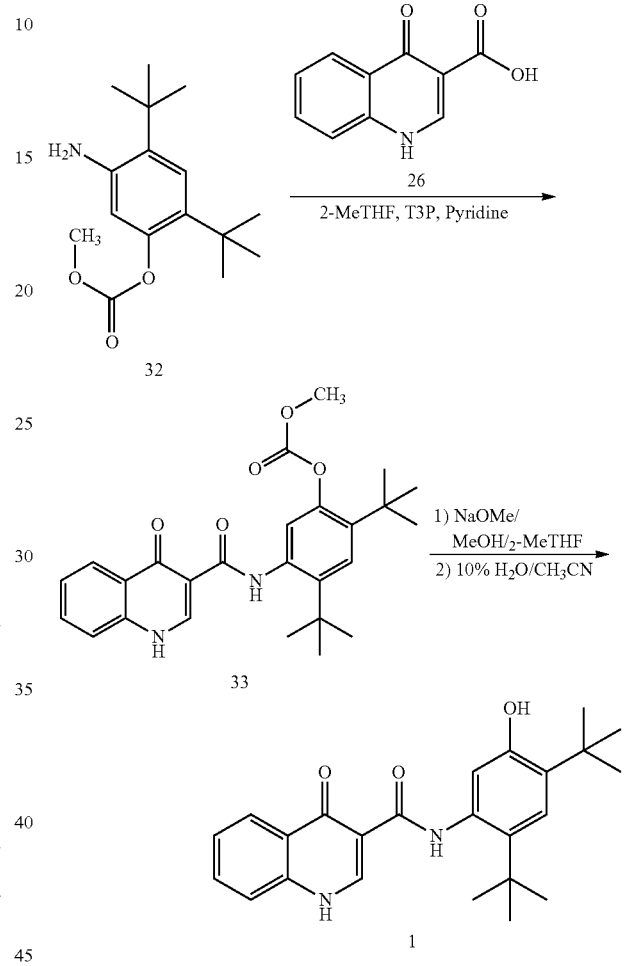

4-Oxo-1,4-dihydroquinoline-3-carboxylic acid, 26, (1.0 eq) and 5-amino-2,4-di-tert-butylphenyl methyl carbonate, 32, (1.1 eq) were charged to a reactor. 2-MeTHF (4.0 vol, relative to the acid) was added followed by T3P® 50% solution in 2-MeTHF (1.7 eq). The T3P charged vessel was washed with 2-MeTHF (0.6 vol). Pyridine (2.0 eq) was then added, and the resulting suspension was heated to 47.5+/−5.0° C. and held at this temperature for 8 hours. A sample was taken and checked for completion by HPLC. Once complete, the resulting mixture was cooled to 20° C.+/−5° C. 2-MeTHF was added (12.5 vol) to dilute the mixture. The reaction mixture was washed with water (10.0 vol) 2 times and 2-MeTHF (16.5 vol) was charged to the reactor. This solution was charged with 30% w/w NaOMe/MeOH (1.7 equiv) to perform the methanolysis. The reaction was stirred at 25.0° C.+/−5.0° C. for no less than 1.0 hour, and checked for completion by HPLC. Once complete, the reaction was quenched with 1.2 N HCl/H$_2$O (10.0 vol), and washed with 0.1 N HCl/H$_2$O (10.0 vol). The organic solution was polish filtered to remove any particulates and placed in a second reactor.

The filtered solution was concentrated at no more than 35° C. (jacket temperature) and no less than 8.0° C. (internal reaction temperature) under reduced pressure to 20 vol. $CH_3CN$ was added to 40 vol and the solution concentrated at no more than 35° C. (jacket temperature) and no less than 8.0° C. (internal reaction temperature) to 20 vol. The addition of $CH_3CN$ and concentration cycle was repeated 2 more times for a total of 3 additions of $CH_3CN$ and 4 concentrations to 20 vol. After the final concentration to 20 vol, 16.0 vol of $CH_3CN$ was charged followed by 4.0 vol of $H_2O$ to make a final concentration of 40 vol of 10% $H_2O/CH_3CN$ relative to the starting acid. This slurry was heated to 78.0° C.+/−5.0° C. (reflux). The slurry was then stirred for no less than 5 hours. The slurry was cooled to 20 to 25° C. over 5 hours, and filtered. The cake was washed with $CH_3CN$ (5 vol) heated to 20 to 25° C. 4 times. The resulting solid (compound 1) was dried in a vacuum oven at 50.0° C.+/−5.0° C. $^1$H NMR (400 MHz, DMSO-$d_6$) δ 12.8 (s, 1H), 11.8 (s, 1H), 9.2 (s, 1H), 8.9 (s, 1H), 8.3 (s, 1H), 7.2 (s, 1H), 7.9 (t, 1H), 7.8 (d, 1H), 7.5 (t, 1H), 7.1 (s, 1H), 1.4 (s, 9H), 1.4 (s, 9H).

Example 3

Procedure for the Recrystallization of N-(2,4-di-tert-butyl-5-hydroxyphenyl)-4-oxo-1,4-dihydroquinoline-3-carboxamide (1)

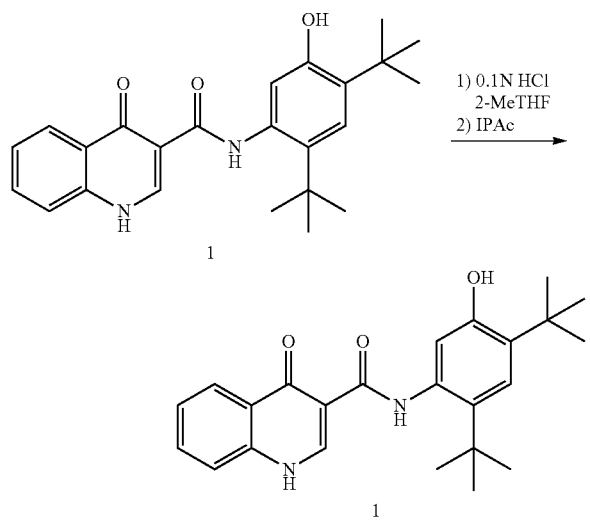

Compound 1 (1.0 eq) was charged to a reactor. 2-MeTHF (20.0 vol) was added followed by 0.1N HCl (5.0 vol). The biphasic solution was stirred and separated and the top organic phase was washed twice more with 0.1N HCl (5.0 vol). The organic solution was polish filtered to remove any particulates and placed in a second reactor. The filtered solution was concentrated at no more than 35° C. (jacket temperature) and no more than 8.0° C. (internal reaction temperature) under reduced pressure to 10 vol. Isopropyl acetate (IPAc) (10 vol) was added and the solution concentrated at no more than 35° C. (jacket temperature) and no more than 8.0° C. (internal reaction temperature) to 10 vol. The addition of IPAc and concentration was repeated 2 more times for a total of 3 additions of IPAc and 4 concentrations to 10 vol. After the final concentration, 10 vol of IPAc was charged and the slurry was heated to reflux and maintained at this temperature for 5 hours. The slurry was cooled to 0.0° C.+/−5° C. over 5 hours and filtered. The cake was washed with IPAc (5 vol) once. The resulting solid was dried in a vacuum oven at 50.0° C.+/−5.0° C.

Methods of Making Compound 1 Form C

Form C of Compound 1 was prepared by adding an excess of Compound 1, prepared as in example 3, into acetonitrile, stirring at 90° C. for 3 days, and cooling to room temperature. The product was harvested by filtration, and the purity of the product was confirmed using SSNMR.

What is claimed is:

1. A method of treating or lessening the severity of a disease in a patient, wherein said disease is selected from cystic fibrosis, smoke induced COPD, pancreatitis, pancreatic insufficiency, hereditary emphysema, COPD, or dry-eye disease, said method comprising the step of administering to said patient an effective amount of crystalline N-[2,4-bis(1,1-dimethylethyl)-5-hydroxyphenyl]-1,4-dihydro-4-oxoquinoline-3-carboxamide characterized as Form C.

2. The method according to claim 1, wherein said disease is cystic fibrosis.

3. The method according to claim 1, wherein the patient possesses one or more of the following mutations of human CFTR: ΔF508, R117H, and G551D.

4. The method according to claim 3, wherein the method includes treating or lessening the severity of cystic fibrosis in a patient possessing the ΔF508 mutation of human CFTR.

5. The method according to claim 3, wherein the method includes treating or lessening the severity of cystic fibrosis in a patient possessing the G551D mutation of human CFTR.

6. The method according to claim 4, wherein the method includes treating or lessening the severity of cystic fibrosis in a patient possessing the ΔF508 mutation of human CFTR on at least one allele.

7. The method according to claim 4, wherein the method includes treating or lessening the severity of cystic fibrosis in a patient possessing the ΔF508 mutation of human CFTR on both alleles.

8. The method according to claim 5 wherein the method includes treating or lessening the severity of cystic fibrosis in a patient possessing the G551D mutation of human CFTR on at least one allele.

9. The method according to claim 5, wherein the method includes treating or lessening the severity of cystic fibrosis in a patient possessing the G551D mutation of human CFTR on both alleles.

* * * * *